United States Patent [19]

Tilley

[11] Patent Number: 4,551,460
[45] Date of Patent: Nov. 5, 1985

[54] PYRIDO[2,1-B]QUINAZOLINE DERIVATIVES USEFUL AS AGENTS FOR TREATMENT OF ALLERGIC CONDITIONS AND VASCULAR DISORDERS INVOLVING THROMBOSIS

[75] Inventor: Jefferson W. Tilley, North Caldwell, N.J.

[73] Assignee: Hoffmann-La Roche Inc., Nutley, N.J.

[21] Appl. No.: 471,382

[22] Filed: Mar. 2, 1983

Related U.S. Application Data

[63] Continuation-in-part of Ser. No. 376,324, May 10, 1982, abandoned.

[51] Int. Cl.$^4$ ............... A61K 31/505; C07D 471/04
[52] U.S. Cl. ............................. 514/267; 514/242; 544/182; 544/242; 544/252; 544/333; 544/335; 546/152; 546/176; 546/272; 546/300; 546/329; 546/330; 546/334; 546/336; 546/340; 546/341; 546/344; 548/336; 548/341; 549/78
[58] Field of Search ............... 544/252, 216, 182; 424/251, 249

[56] References Cited

U.S. PATENT DOCUMENTS

| 4,011,324 | 3/1977 | Althuis | 424/251 |
| 4,018,931 | 4/1977 | Durant et al. | 424/269 |
| 4,033,961 | 7/1977 | Schwender et al. | 544/252 |
| 4,065,566 | 12/1977 | Bodor et al. | 424/266 |
| 4,066,767 | 1/1978 | Schwender et al. | 424/251 |
| 4,083,980 | 4/1978 | Schromm et al. | 424/251 |
| 4,104,389 | 8/1978 | Schwender et al. | 424/251 |
| 4,272,535 | 6/1981 | Blythin | 424/248.54 |
| 4,275,064 | 6/1981 | Bodor et al. | 424/253 |
| 4,348,396 | 9/1982 | Kierstead et al. | 424/251 |
| 4,376,767 | 3/1983 | Sloan | 424/232 |

OTHER PUBLICATIONS

Tilley, et al., J. Med. Chem., vol. 26, No. 11, pp. 1638–1642 (11/83).
Yanouchi, et al., J. Med. Chem., vol. 24, No. 10, pp. 1149–1155 (1981).
Iizuka, et al., J. Med. Chem., vol. 24, No. 10, pp. 1139–1148 (1981).
LeMahieu, et al., J. Med. Chem., vol. 26, No. 3, pp. 420–425 (1983).
Tilley, et al., Chemical Abstracts, vol. 99, 158374d (1983).

Primary Examiner—Donald G. Daus
Assistant Examiner—Diana G. Rivers
Attorney, Agent, or Firm—Jon S. Saxe; Bernard S. Leon; Matthew Boxer

[57] ABSTRACT

Pyrido[2,1-b]quinazoline derivatives of the formulas

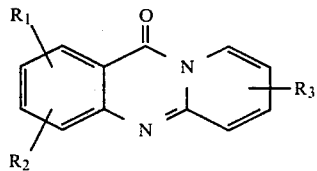

and

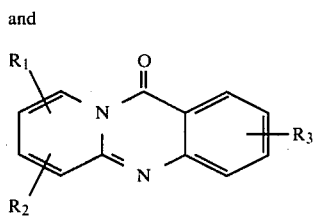

wherein $R_1$, $R_2$ and $R_3$ are as hereinafter set forth, are described. The compounds of formulas I and II are useful as agents for the treatment of allergic conditions as well as for the treatment of vascular disorders involving thrombosis.

58 Claims, No Drawings

PYRIDO[2,1-B]QUINAZOLINE DERIVATIVES USEFUL AS AGENTS FOR TREATMENT OF ALLERGIC CONDITIONS AND VASCULAR DISORDERS INVOLVING THROMBOSIS

RELATED APPLICATIONS

This application is a continuation-in-part of application Ser. No. 376,324, filed May 10, 1982, abandoned.

BRIEF SUMMARY OF THE INVENTION

The invention relates to compounds of the formula

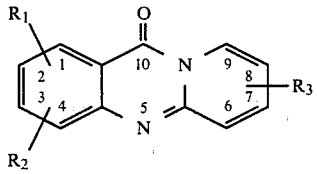
I wherein $R_1$ and $R_2$, independently, are hydrogen, lower alkyl, lower alkoxy, hydroxy or halogen, and $R_3$ is in the 6-, 7- or 8-ring position and is

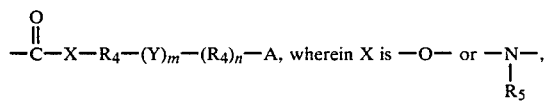

wherein $R_5$ is hydrogen or lower alkyl, $R_4$ is lower alkylene, Y is —O— or —S—, m is zero or 1, n is zero or 1, and A is an unsubstituted or substituted aromatic 5- or 6-membered heterocyclic group, provided that when A is linked through a heterocyclic nitrogen, m and n must be zero, and compounds of the formula

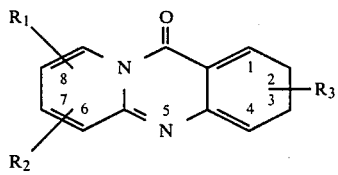
II wherein $R_1$ and $R_2$, independently, are hydrogen, lower alkyl, lower alkoxy, hydroxy or halogen, and $R_3$ is in the 2-, 3- or 4-position and is

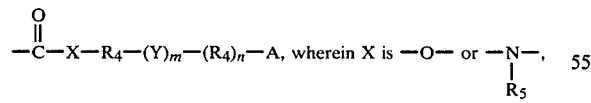

wherein $R_5$ is hydrogen or lower alkyl, $R_4$ is lower alkylene, Y is —O— or —S—, m is zero or 1, n is zero or 1, and A is an unsubstituted or substituted aromatic 5- or 6-membered heterocyclic group, provided that when A is linked through a heterocyclic nitrogen, m and n must each be zero, and pharmaceutically acceptable acid addition salts thereof.

In still aother aspect, the invention relates to intermediates for the preparation of the compounds of formulas I and II.

DETAILED DESCRIPTION OF THE INVENTION

As used herein, the term "lower alkyl" denotes a straight or branched chain saturated hydrocarbon containing 1 to 7 carbon atoms, for example, methyl, ethyl, propyl, isopropyl, butyl, t-butyl, neopentyl, pentyl, heptyl and the like. The term "lower alkylene" denotes a hydrocarbon radical of 2 to 7 carbon atoms, preferably of 4 to 6 carbon atoms, such as ethylene, propylene, butylene and pentylene, which may be substituted by one or more lower alkyl groups, for example, 1-methylpropylene, 1-methyl-butylene or the like. The term "lower alkoxy" denotes an alkyl ether group in which the lower alkyl group is as described above, for example, methoxy, ethoxy, propoxy, pentoxy and the like. The term "halogen" denotes all the halogens, that is, bromine, chlorine, fluorine and iodine.

The term "heterocyclic group" denotes a 5- or 6-membered heterocyclic ring unsubstituted or substituted, which may be fused to another 6-membered heterocyclic or non-heterocyclic ring, especially heteroaromatic rings which contain 1 to 3, or particularly 1 or 2, hetero-atoms which may be the same or different. Nitrogen, oxygen and sulfur are the preferred hetero-atoms. A substituted heterocyclic group may be substituted by one or more, preferably 1 or 2, substituents which may be the same or different. Preferred substituents are straight- and branched-chain lower alkyl, especially of 1 or 2 carbon atoms; straight- and branched-chain lower alkoxy, especially of 1 or 2 carbon atoms; halogen; and nitro.

Preferred heterocyclic rings are pyridyl, pyrimidinyl, imidazolyl, furyl, thiazolyl, oxazolyl, isoxazolyl, pyrazinyl, quinolinyl, isoquinolinyl, quinazolinyl, 1,2,4-triazinyl, benzimidazolyl and pyridazinyl. These rings can be linked, for example, through a carbon atom or nitrogen atom as indicated below.

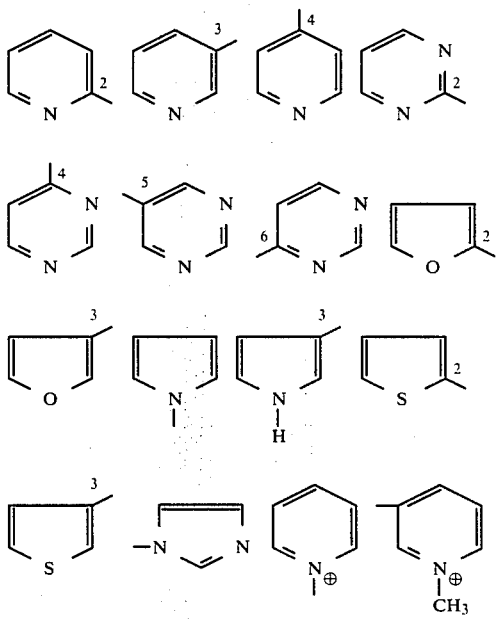

In one aspect the invention relates to compounds of the formula

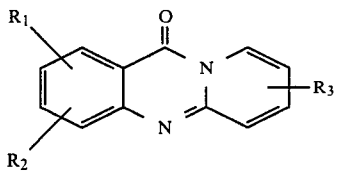

wherein $R_1$ and $R_2$, independently, are hydrogen, lower alkyl, lower alkoxy, hydroxy or halogen and $R_3$ is in the 6-, 7- or 8-ring position and is

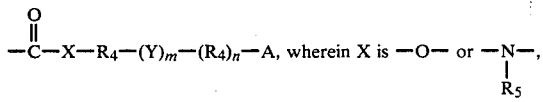

wherein $R_5$ is hydrogen or lower alkyl, $R_4$ is lower alkylene, Y is —O— or —S—, m is zero or 1, n is zero or 1, and A is an unsubstituted or substituted aromatic 5- or 6-membered heterocyclic group, provided that when A is linked through a heterocyclic nitrogen, m and n must be zero, and pharmaceutically acceptable acid addition salts thereof.

In another aspect the invention relates to compounds of the formula

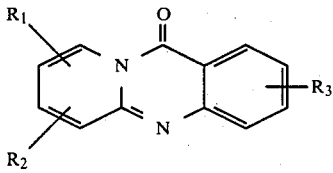

wherein $R_1$ and $R_2$, independently, are hydrogen, lower alkyl, lower alkoxy, hydroxy or halogen, and $R_3$ is in the 2-, 3- or 4-position and is

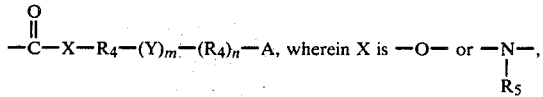

wherein $R_5$ is hydrogen or lower alkyl, $R_4$ is lower alkylene, Y is —O— or —S—, m is zero or 1, n is zero or 1, A is an unsubstituted or substituted aromatic 5- or 6-membered heterocyclic group, provided that when A is linked through a heterocyclic nitrogen, m and n must each be zero, and pharmaceutically acceptable acid addition salts thereof.

Preferred compounds of formula I are those wherein X is

More preferred compounds of formula I are those wherein X is

and A is 3-pyridyl, 4-pyridyl or imidazol-1-yl.

Still more preferred compounds of formula I are those wherein X is

A is 3-pyridyl, 4-pyridyl or imidazol-1-yl, and $R_1$ and $R_2$ are in the 2- and 3-position, respectively, and $R_3$ is the 8-position.

A most preferred group of compounds of formula I are those wherein $R_3$ is in the 8-position, X is

A is 3-pyridyl, 4-pyridyl or imidazol-1-yl, $R_1$ is lower alkyl and in the 2-position, $R_2$ is hydrogen; $R_4$ is lower alkylene of 4–6 carbon atoms, and m and n are zero.

Preferred compounds of formula II are those wherein X is

More preferred compounds of formula II are those wherein X is

and A is 3-pyridyl, 4-pyridyl or imidazol-1-yl.

Still more preferred compounds of formula II are those wherein X is

A is 3-pyridyl, 4-pyridyl or imidazol-1-yl, and $R_1$ and $R_2$ are in the 8- and 7-position, respectively, and $R_3$ is in the 2-position.

A most preferred group of compounds of formula II are those wherein $R_3$ is in the 2-position, X is

A is 3-pyridyl, 4-pyridyl or imidazol-1-yl, $R_1$ is lower alkyl and in the 8-position, $R_2$ is hydrogen, $R_4$ is lower alkylene of 4–6 carbon atoms, and m and n are zero.

Most preferred compounds of formula I are:
N-[4-(1H-imidazol-1-yl)butyl]-2-(1-methylethyl)-11-oxo-11H-pyrido[2,1-b]quinazoline-8-carboxamide;
2-(1-Methylethyl)-N-[6-(3-pyridyl)hexyl]-11-oxo-11H-pyrido[2,1-b]quinazoline-8-carboxamide; and
2-(1-Methylethyl)-N-[4-(3-pyridyl)butyl]-11-oxo-11H-pyrido[2,1-b]quinazoline-8-carboxamide.

Most preferred compounds of formula II are:
8-(1-Methylethyl)-N-[4-(3-pyridyl)butyl]-11-oxo-11H-pyrido[2,1-b]quinazoline-2-carboxamide; N-[4-(1H-imidazol-1-yl)butyl]-8-(1-methylethyl)-11-oxo-11H-pyrido[2,1-b]quinazoline-2-carboxamide; and 8-(1-Methylethyl)-N-[6-(3-pyridyl)hexyl]-11-oxo-11H-pyrido[2,1-b]quinazoline-2-carboxamide.

Exemplary of the compounds of formula I of the invention are:

N-[4-(4-Pyridyl)butyl-2-(1-methylethyl)-11-oxo-11H-pyrido[2,1-b]quinazoline-8-carboxamide;
N-[2-(2-Pyridyl)ethyl]-2-(1-methylethyl)-11-oxo-11H-pyrido[2,1-b]quinazoline-8-carboxamide;
N-[2-(3-Pyridyl)ethyl]-2-(1-methylethyl)-11-oxo-11H-pyrido[2,1-b]quinazoline-8-carboxamide;
N-[3-(3-Pyridyl)propyl]-2-(1-methylethyl)-11-oxo-11H-pyrido[2,1-b]quinazoline-8-carboxamide;
N-[5-(1H-Imidazol-1-yl)pentyl]-2-(1-methylethyl)-11-oxo-11H-pyrido[2,1-b]quinazoline-8-carboxamide;
N-[3-(1H-Imidazol-1-yl)propyl]-2-(1-methylethyl)-11-oxo-11H-pyrido[2,1-b]quinazoline-8-carboxamide;
N-Methyl-2-(1-methylethyl)-N-[4-(3-pyridyl)butyl]-11-oxo-11H-pyrido[2,1-b]quinazoline-8-carboxamide;
2-(1-Methylethyl)-11-oxo-11H-pyrido[2,1-b]quinazoline-8-carboxylic acid 3-(3-pyridinyl)propyl ester;
N-[2-(4-Pyridylthio)ethyl]-2-(1-methylethyl)-11-oxo-11H-pyrido[2,1-b]quinazoline-8-carboxamide;
2-(1-Methylethyl)-N-[4-(3-pyridyloxy)butyl]-11-oxo-11H-pyrido[2,1-b]quinazoline-8-carboxamide;
N-[5-(3-Pyridyl)pentyl]-2-(1-methylethyl)-11-oxo-11H-pyrido[2,1-b]quinazoline-8-carboxamide;
2-(1-Methylethyl)-N-[4-(4-pyridylthio)butyl]-11-oxo-11H-pyrido[2,1-b]quinazoline-8-carboxamide;
2-Methoxy-N-[4-(3-pyridyl)butyl]-11-oxo-11H-pyrido[2,1-b]quinazoline-8-carboxamide;
2-(1-Methylethoxy)-N-[4-(3-pyridyl)butyl]-11-oxo-11H-pyrido[2,1-b]quinazoline-8-carboxamide;
2-Methyl-N-[4-(3-pyridyl)butyl]-11-oxo-11H-pyrido[2,1-b]quinazoline-8-carboxamide;
N-[5-(4-Pyridyl)pentyl]-2-(1-methylethyl)-11-oxo-11H-pyrido[2,1-b]quinazoline-8-carboxamide;
2-(1-Methylethyl)-N-[4-(2-pyridyl)butyl]-11-oxo-11H-pyrido[2,1-b]quinazoline-8-carboxamide;
2-(1-Methylethyl)-N-[7-(3-pyridyl)heptyl]-11-oxo-11H-pyrido[2,1-b]quinazoline-8-carboxamide;
2-(1-Methylethyl)-N-[2-[[(4-pyridyl)methyl]thio]ethyl]-11-oxo-11H-pyrido[2,1-b]quinazoline-8-carboxamide;
2-(1-Methylethyl)-n-[2-[[(3-pyridyl)methyl]thio]ethyl]-11-oxo-11H-pyrido[2,1-b]quinazoline-8-carboxamide;
N-[6-(1H-Imidazol-1-yl)hexyl]-2-(1-methylethyl)-11-oxo-11H-pyrido[2,1-b]quinazoline-8carboxamide;
N-[4-(2-Methyl-1H-imidazol-1-yl)butyl]-2-(1-methylethyl)-11-oxo-11H-pyrido[2,1-b]quinazoline-8-carboxamide;
N-[4-(3-Pyridyl)butyl]-11-oxo-11H-pyrido[2,1-b]quinazoline-8-carboxamide;
2-(1-Methylethyl)-N-[4-(3-pyridyl)butyl]-11-oxo-11H-pyrido[2,1-b]quinazoline-6-carboxamide;
2-Hydroxy-N-[4-(3-pyridyl)butyl]-11-oxo-11H-pyrido[2,1-b]quinazoline-8-carboxamide;
2-Bromo-N-[4-(3-pyridyl)butyl]-11-oxo-11H-pyrido[2,1-b]quinazoline-8-carboxamide;
3-Chloro-N-[4-(3-pyridyl)butyl]-11-oxo-11H-pyrido[2,1-b]quinazoline-8-carboxamide;
3-Methoxy-N-[4-(3-pyridyl)butyl]-11-oxo-11H-pyrido[2,1-b]quinazoline-8-carboxamide;
2,3-Dimethyl-N-[4-(3-pyridyl)butyl]-11-oxo-11H-pyrido[2,1-b]quinazoline-8-carboxamide;
2-(1-Methylethyl)-N-[1-methyl-3-(3-pyridyl)propyl]-11-oxo-11H-pyrido[2,1-b]quinazoline-8-carboxamide;
2-(1-Methylethyl)-N-[4-(5-pyrimidinyl)butyl]-11-oxo-11H-pyrido[2,1-b]quinazoline-8-carboxamide;
2-(1-Methylethyl)-N-[2-(2-pyridylthio)ethyl]-11-oxo-11H-pyrido[2,1-b]quinazoline-8-carboxamide;
2-(1-Methylethyl)-N-[4-(4-isoquinolyl)butyl]-11-oxo-11H-pyrido[2,1-b]quinazoline-8-carboxamide;
2-(1-Methylethyl)-N-[6-(3-quinolyl)hexyl-11-oxo-11H-pyrido[2,1-b]quinazoline-8-carboxamide;
2-(1-Methylethyl)-N-[6-(3-thienyl)hexyl-11-oxo-11H-pyrido[2,1-b]quinazoline-8-carboxamide;
2-(1-Methylethyl)-N-[4-(5-oxazolyl)butyl]-11-oxo-11H-pyrido[2,1-b]quinazoline-8-carboxamide;
2-(1-Methylethyl)-N-[4-(4-thiazolyl)butyl]-11-oxo-11H-pyrido[2,1-b]quinazoline-8-carboxamide;
2-Methoxy-N-[6-(3-pyridyl)hexyl]-11-oxo-11H-pyrido[2,1-b]quinazoline-6-carboxamide;
2-Methoxy-N-[4-(3-pyridyl)butyl]-11-oxo-11H-pyrido[2,1-b]quinazoline-6-carboxamide;
2-(1-Methylethyl)-N-[4-(3-pyridyl)butyl]-11-oxo-11H-pyrido[2,1-b]quinazoline-7-carboxamide;
2-(1-Methylethyl)-N-[4-(1H-imidazol-1-yl)butyl]-11-oxo-11H-pyrido[2,1-b]quinazoline-7-carboxamide;
2-Methoxy-N-[4-(1H-imidazol-1-yl)butyl]-11-oxo-11H-pyrido[2,1-b]quinazoline-7-carboxamide;
2-(1-Methylethyl)-N-[4-(1H-1,2,4-triazol-1-yl)butyl]-11-oxo-11H-pyrido[2,1-b]quinazoline-8-carboxamide;
2-(1-Methylethyl)-N-[2-(4-purimidinylthio)ethyl]-11-oxo-11H-pyrido[2,1-b]quinazoline-8-carboxamide;
2-Hydroxy-N-[6-(3-pyridyl)hexyl]-11-oxo-11H-pyrido[2,1-b]quinazoline-8-carboxamide;
2-Hydroxy-N-[4-(1H-imidazol-1-yl)butyl]-11-oxo-11H-pyrido[2,1-b]quinazoline-8-carboxamide;
4-Methoxy-N-[4-(1H-imidazol-1-yl)butyl]-11-oxo-11H-pyrido[2,1-b]quinazoline-8-carboxamide;
4-Chloro-N-[4-(1H-imidazol-1-yl)butyl]-11-oxo-11H-pyrido[2,1-b]quinazoline-8-carboxamide;
4-Methyl-N-[4-(1H-imidazol-1-yl)butyl]-11-oxo-11H-pyrido[2,1-b]quinazoline-8-carboxamide;
2-Butyl-N-[4-(1H-imidazol-1-yl)butyl]-11-oxo-11H-pyrido[2,1-b]quinazoline-8-carboxamide;
2-(1-Methylethyl)-11-oxo-11H-pyrido[2,1-b]quinazoline-8-carboxylic acid 4-(3-pyridinyl)butyl ester;
2-(1-Methylethoxy)-N-[6-(3-pyridyl)hexyl]-11-oxo-11H-pyrido[2,1-b]quinazoline-8-carboxamide;
2-(1-Methylethoxy)-N-[6-(5-pyrimidinyl)hexyl]-11-oxo-11H-pyrido[2,1-b]quinazoline-8-carboxamide;
2,3-Dimethyl-N-[6-(3-pyridyl)hexyl]-11-oxo-11H-pyrido[2,1-b]quinazoline-8-carboxamide;
2,3-Dimethyl-N-[4-(5-pyrimidinyl)butyl]-11-oxo-11H-pyrido[2,1-b]quinazoline-8-carboxamide;
2-(1-Methylethyl)-N-[1-methyl-3-(5-pyrimidinyl)propyl]-11-oxo-11H-pyrido[2,1-b]quinazoline-8-carboxamide;
2-(1-Methylethyl)-N-[1-methyl-4-(3-pyridyl)butyl]-11-oxo-11H-pyrido[2,1-b]quinazoline-8-carboxamide;
2-(1-Methylethyl)-N-[1-methyl-3-(3-pyridyl)propyl]-11-oxo-11H-pyrido[2,1-b]quinazoline-8-carboxamide;
2-(1-Methylethyl)-N-methyl-N-[4-(1H-imidazol-1-yl)butyl]-11-oxo-11H-pyrido[2,1-b]quinazoline-8-carboxamide;
2-(1-Methylethyl)-N-[1-methyl-4-(1H-imidazol-1-yl)butyl]-11-oxo-11H-pyrido[2,1-b]quinazoline-8-carboxamide;
2-(1-Methylethyl)-N-methyl-N-[1-methyl-4-(1H-imidazol-1-yl)butyl]-11-oxo-11H-pyrido[2,1-b]-quinazoline-8-carboxamide;
1-[3-[[(2,3-Dimethyl-11-oxo-11H-pyrido[2,1-b]quinazolin-8-yl)carbonyl]amino]propyl]pyridinium chloride;
1-[4-[[(2,3-Dimethyl-11-oxo-11H-pyrido[2,1-b]quinazolin-8-yl)carbonyl]amino]butyl]pyridinium chloride;

3-[4-[[(2,3-Dimethyl-11-oxo-11H-pyrido[2,1-b]-quinazolin-8-yl)carbonyl]amino]butyl]-1-methyl-pyridinium iodide; and the like.

Exemplary of the compounds of formula II of the invention are:

8-Methyl-N-[6-(4-pyridyl)hexyl]-11-oxo-11H-pyrido[2,1-b]quinazoline-2-carboxamide;

8-(1-Methylethyl)-11-oxo-11H-pyrido[2,1-b]quinazoline-2-carboxylic acid 3-(3-pyridyl)propyl ester;

8-Chloro-N-[4-(1H-imidazol-1-yl)butyl]-11-oxo-11H-pyrido[2,1-b]quinazoline-2-carboxamide;

8-Chloro-11-oxo-11H-pyrido[2,1-b]quinazoline-2-carboxylic acid 3-(3-pyridyl)propyl ester; and the like.

The compounds of formula I of the invention can be prepared in accordance with Reaction Schemes I–IV which follow:

Reaction Scheme I

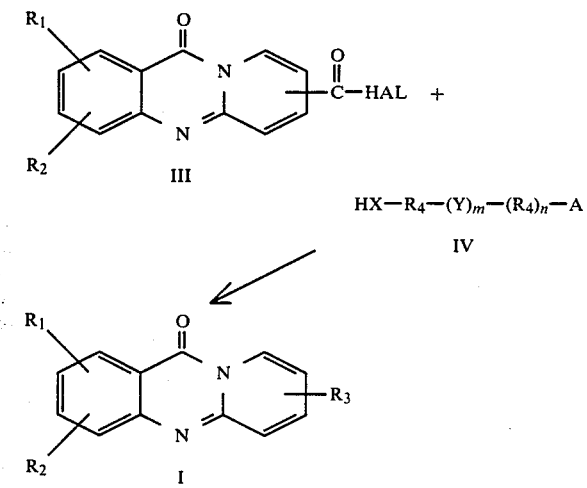

wherein $R_1$, $R_2$, $R_3$, $R_4$, A, X, Y, m and n are as previously described, and HAL is halogen.

In Reaction Scheme I, the reaction of an acid halide of formula III with a compound of formula IV can be carried out with or without a solvent. Exemplary of the solvent, which can be utilized are aprotic solvents such as dimethylformamide, hexamethylphosphoramide, N-methylpyrrolidinone, acetonitrile, toluene or the like. Preferably, the reaction is carried out at a temperature in the range of 0° to the reflux temperature of the reaction mixture. The resulting compound of formula I can be recovered utilizing conventional methods, for example, crystallization, chromatography or the like.

Reaction Scheme II

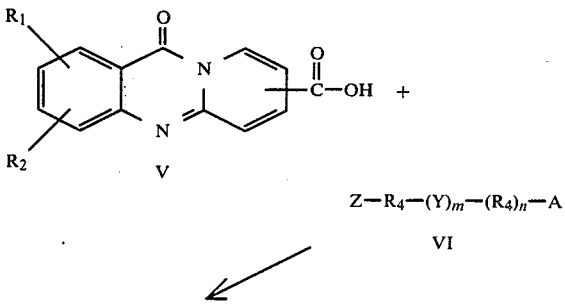

-continued
Reaction Scheme II

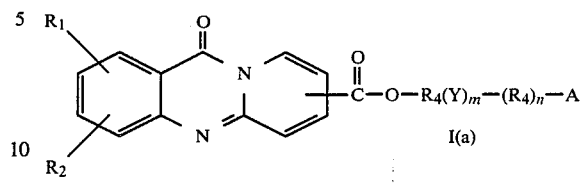

wherein $R_1$, $R_2$, $R_4$, A, Y, m and n are as previously described, and Z is a leaving group, such as, halogen, tosyl, mesyl or the like.

In Reaction Scheme II, the reaction of an acid of formula V with a compound of formula VI can be carried out in a polar, aprotic solvent such as dimethylformamide, hexamethylphosphoramide, acetonitrile or the like at a reaction temperature in the range of 0° to 100° in the presence of a base such as an alkali metal carbonate. The resulting compound of formula I(a) can be recovered utilizing conventional methods, for example, crystallization, chromatography or the like.

Reaction Scheme III

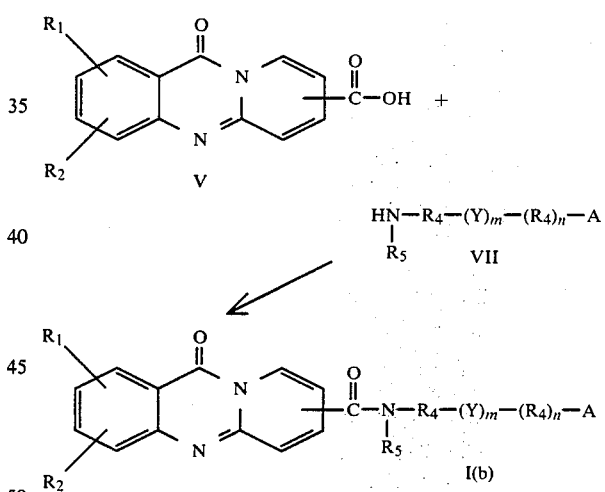

wherein $R_1$, $R_2$, $R_4$, $R_5$, A, Y, m and n are as previously described.

In Reaction Scheme III, the reaction of an acid of formula V with an amine of formula VII can be carried out in a polar, aprotic solvent such as dimethylformamide, hexamethylphosphoramide, N-methylpyrrolidinone or the like, in the presence of diphenylphosphoryl azide at a reaction temperature in the range of 0° to room temperature. The reaction is carried out in the presence of a proton-acceptor, that is, a base, for example, a trialkylamine such as triethylamine or the like. The resulting compound of formula I(b) can be recovered utilizing conventional methods, for example, crystallization, chromatography or the like.

Reaction Scheme IV

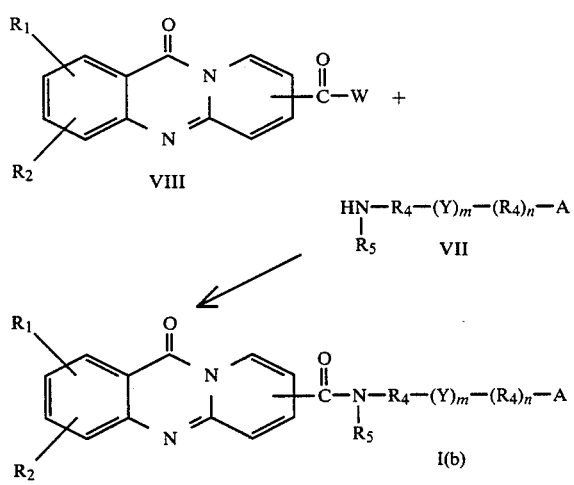

wherein $R_1$, $R_2$, $R_4$, $R_5$, A, Y, m and n are as previously described, and W is cyanomethoxy, phenyloxy or the like.

In Reaction Scheme IV, the reaction of an ester of formula VIII with an amine of formula VII is carried out in a polar, aprotic solvent such as dimethylformamide, hexamethylphosphoramide, N-methylpyrrolidinone or the like, at a reaction temperature in the range of room temperature to 100°. The resulting compound of formula I(b) can be recovered utilizing conventional methods, for example, crystallization, chromatography or the like.

The compounds of formula II of the invention can be prepared in accordance with Reaction Schemes V and VI which follow:

Reaction Scheme V

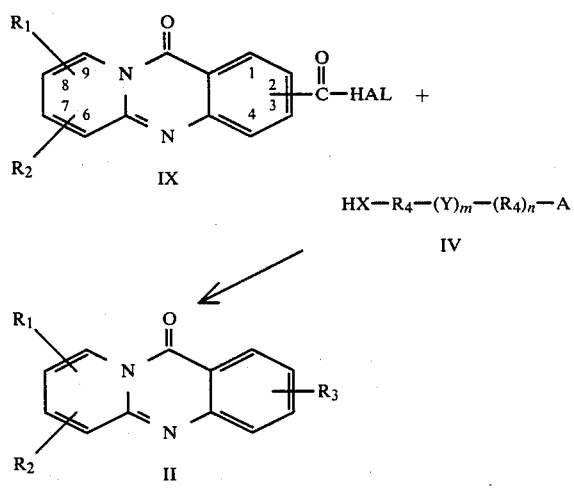

wherein $R_1$, $R_2$, $R_3$ and $R_4$ are as previously described, and HAL is halogen.

In Reaction Scheme V, the reaction of an acid halide of formula IX with a compound of formula IV can be carried out with or without a solvent. Exemplary of the solvents which can be utilized are aprotic solvents such as dimethylformamide, hexamethylphosphoramide, N-methylpyrrolidinone, acetonitrile, toluene or the like. Preferably, the reaction is carried out at a temperature in the range of 0° to the reflux temperature of the reaction mixture. The resulting compound of formula II can be recovered utilizing conventional methods, for example, crystallization, chromatography or the like.

Reaction Scheme VI

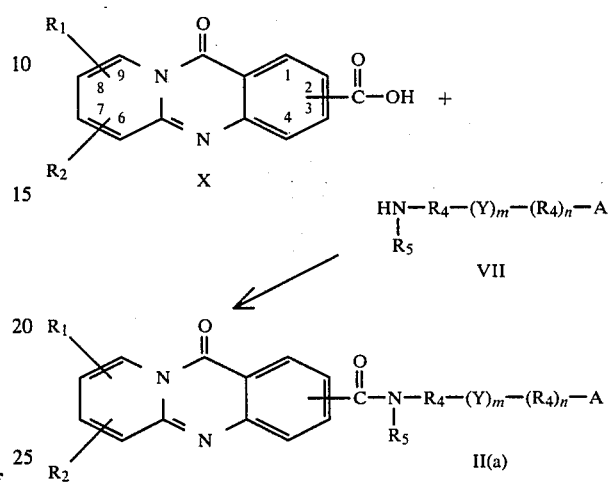

wherein $R_1$, $R_2$, $R_4$, $R_5$, A, Y, m and n are as previously described.

In Reaction Scheme VI, the reaction of an acid of formula X with an amine of formula VII can be carried out in a polar, aprotic solvent such as dimethylformamide, hexamethylphosphoramide, N-methylpyrrolidinone or the like, in the presence of diphenylphosphoryl azide at a reaction temperature in the range of 0° to room temperature. The reaction is carried out in the presence of a proton-acceptor, for instance, a base, for example, a trialkylamine such as triethylamine or the like. The resulting compound of formula II(a) can be recovered utilizing conventional methods, for example, crystallization, chromatography or the like.

The starting materials of the formula

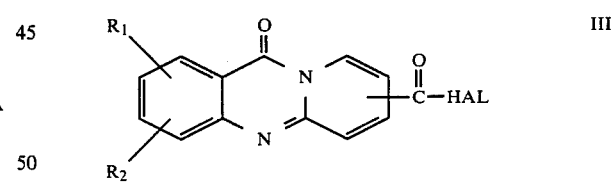

wherein $R_1$, $R_2$ and HAL are as herein described, are known compounds or can be prepared according to known procedures.

Exemplary of the compounds of the formula III are:
2-(1-Methylethyl)-1-oxo-11H-pyrido[2,1-b]quinazoline-8-chlorocarbonyl;
2-Methoxy-11-oxo-11H-pyrido[2,1-b]quinazoline-8-chlorocarbonyl;
2-Bromo-11-oxo-11H-pyrido[2,1-b]quinazoline-8-chlorocarbonyl;
2-Methyl-11-oxo-11H-pyrido[2,1-b]quinazoline-8-chlorocarbonyl; and the like.

The starting materials of formula $$HX-R_4-(Y)_m-(R_4)_n-A \qquad IV$$

wherein R4, X, Y m, n, and A is as herein described, are known compounds or can be prepared according to known procedures.

Exemplary of the compounds of formula IV are:
3-(3-Hydroxypropyl)pyridine;
1-(4-Hydroxybutyl)-1H-imidazole;
4-(3-Hydroxypropyl)pyridine;
3-(6-Hydroxyhexyl)pyridine;
3-Pyridine-N-methylbutanamine;
1-Methyl-3-(3-pyridinyl)propanamine;
1-Methyl-3-(5-pyrimidinyl)propanamine;
5-(4-Hydroxylbutyl)pyrimidine; and the like.

The starting materials of the formula

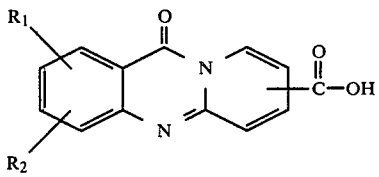                                         V wherein $R_1$ and $R_2$ are as herein described, are known compounds or can be prepared according to known procedures.

Exemplary of the compounds of formula V are:
2-Methyl-11-oxo-11H-pyrido[2,1-b]quinazoline-8-carboxylic acid;
2-(1-Methylethyl)-11-oxo-11H-pyrido[2,1-b]quinazoline-8-carboxylic acid;
2-Methoxy-11-oxo-11H-pyrido[2,1-b]quinazoline-8-carboxylic acid;
2-(1-Methylethyl)-11-oxo-11H-pyrido[2,1-b]quinazoline-6-carboxylic acid;
2-(1-Methylethyl)-11-oxo-11H-pyrido[2,1-b]quinazoline-7-carboxylic acid; and the like.

The starting materials of formula

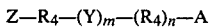    VI wherein R4, A, Y, Z, m and n are as herein described, are known compounds or can be prepared according to known procedures.

Exemplary of the compounds of formula VI are:
3-(3-Bromopropyl)pyridine;
4-(3-Bromopropyl)pyridine;
3-(6-Bromohexyl)pyridine;
3-(3-Methanesulfonylpropyl)pyridine; and the like.

The starting materials of the formula

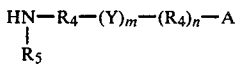    VII wherein R4, R5, A, Y, m and n are as herein described, are known compounds or can be prepared according to known procedures.

Exemplary of the compounds of formula VII are:
3-Pyridinebutanamine;
6-Pyridinehexanamine;
2-[[(3-Pyridinyl]thio]ethanamine;
4-(3-Pyridinyloxy)butanamine;
4-Pyridinebutanamine;
4-(1H-Imidazol-yl)butanamine;
4-(2-Methyl-1H-imidazol-1-yl)butanamine;
5-Pyrimidinebutanamine; and the like.

The starting materials of the formula

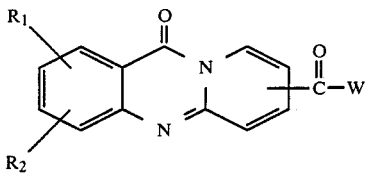                                    VIII wherein W is cyanomethoxy can be prepared by reaction of a compound of formula V with a haloacetonitrile such as chloroacetonitrile in a polar, aprotic solvent such as dimethylformamide, hexamethylphosphoramide, N-methylpyrrolidinone or the like in the presence of a base such as potassium carbonate, sodium carbonate or the like at a temperature of between 0° C. and 50° C.

The starting materials of formula VIII, wherein W is phenoxy or substituted phenoxy can be prepared by reaction of a compound of formula V with a phenol in the presence of an acid halide such as toluene sulfonyl chloride in a polar, aprotic solvent such as dimethylformamide or the like at a temperature of between room temperature and 70° C.

The compounds of formulas I and II above are basic compounds which form acid addition salts with inorganic or organic acids. More particularly, the compounds of formulas I and II form, with pharmaceutically acceptable organic or inorganic acids, pharmaceutically acceptable acid addition salts, for example, hydrohalides such as hydrochloride, hydrobromide or hydroiodide, other mineral acid salts such as sulfate, nitrate, phosphate or the like, alkyl- and mono-aryl sulfonates such as ethanesulfonate, toluenesulfonate, benzenesulfonate, or the like, other organic acid salts such as acetate, tartrate, maleate, citrate, benzoate, salicylate, ascorbate, or the like. Non-pharmaceutically acceptable acid addition salts of the compounds of formulas I and II above can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable anion, The compounds of formulas I and II, including their salts, are antagonist of bronchoconstriction induced by slow reacting substance of anaphylaxis (SRS-A) and other allergic mediators, such as histamine and platelet activating factor. In addition, the compounds of formulas I and II, including their salts, inhibit allergic mediator release and the production of thromboxane $A_2$ through the inhibition of thromboxane synthase. Accordingly, the compounds of formulas I and II, including their salts, are useful as agents for the treatment of allergic conditions which include skin afflictions, hay fever, chronic bronchitis, obstructive airways diseases such as asthma, allergic conditions of the eye, and allergic conditions of the gastro-intestinal tract, such as food allergies, as well as for the treatment of vascular disorders involving thrombosis (platelet aggregation), such as, ischemic heart disease, pulmonary hypertension or the like.

The useful antiallergic activity and antithrombotic activity of the compounds of formulas I and II, including their salts, can be demonstrated in vitro and in warm-blooded animals utilizing standard procedures. Exemplary of such procedures are:

(a) Methodology for LTE-induced Skin Wheal Formation in Rat.

The ability of a drug to inhibit leukotriene E (LTE) induced skin wheal formation in rat skin is measured. In this model system a dose of LTE which gives a maximal wheal response, is injected (in 0.05 ml of saline) intradermally into anesthetized rats which have been pretreated for 30 minutes with 50 mg/kg of pyrilamine maleate and 4 mg/kg of methyl sergide maleate (both administered intraperitoneally). The animal is then immediately treated with test drug (at 10 mg/kg, i.v.) followed by an intravenous injection of Evans blue (0.5%) into the tail vein of the animal. Thirty minutes later the animals are sacrificed and the increase in capillary permeability induced by LTE is reflected by the migration of dye into the injection point in the skin (the response being quantitated by the size, in mm, of the dye spot in the skin). The average response in 5 animals (4 intradermal injections of LTE per animal) treated with the test compound is compared with the response elicited in a similar group of animals which were not treated with the drug. For oral studies, the test animals are pretreated two hours prior to intradermal injection of LTE. In this model system FPL 55712 elicits 88% inhibition at 10 mg/kg, i.v., and is inactive orally.

When N-[4-(1H-imidazol-1-yl)butyl]-2-(1-methylethyl)-11-oxo-11H-pyrido[2,1-b]quinazoline-8-carboxamide, which demonstrated an $LD_{50}$, in mice, of 775 mg/kg orally and 22 mg/kg intraperitoneally, was utilized as the test substance, an $ID_{50}$ of 46 mg/kg, p.o. and an $ID_{50}$ of 30 mg/kg, i.v. were obtained.

When 2-(1-methylethyl)-N-[4-(3-pyridyl)butyl]-11-oxo-11H-pyrido[2,1-b]quinazoline-8-carboxamide, which demonstrated an $LD_{50}$, in mice, of >1000 mg/kg, orally, was utilized as the test substance, an $ID_{50}$ of 70 mg/kg, p.o. and an $ID_{50}$ of 15 mg/kg, i.v. were obtained.

When 2-(1-methylethyl)-N-[4-(4-pyridyl)butyl]-11-oxo-11H-pyrido[2,1-b]quinazoline-8-carboxamide, which demonstrated an $LD_{50}$, in mice of >1000 mg/kg, orally, was utilized as the test substance, an $ID_{50}$ of 90 mg/kg, orally, and an $ID_{50}$ of 10 mg/kg, i.v. were obtained.

(b) LTE-Induced Bronchoconstriction, In Guinea Pigs, In Vivo:

Male guinea pigs (Hartley strain) weighing 300 to 450 grams are anesthetized with urethane (2 g/kg) intraperitoneally and a polyethylene cannula is inserted into the jugular vein for intravenous drug administration. Tracheal pressure is recorded from a cannula inserted in the trachea and connected to a Statham pressure transducer. Respiration is paralyzed with succinyl choline (1.2 mg/kg, i.v.) and the animals are mechanically respirated (Harvard rodent respirator) at 40 breaths/minute and 2.5 cc tidal volume. Two minutes thereafter, propranolol (0.1 mg/kg, i.v.) is administered. Five minutes later, the animals are pretreated intravenously for 30 seconds (at 10 mg/kg) with test drug or control vehicle. The animals are subsequently challenged with a maximally constrictory dose of leukotriene E also administered intravenously. The change (cm $H_2O$) between pre and peak ventilatory pressure readings is averaged for three control animals and five drug treated animals. The percent inhibition is calculated from the following formula: (Control-Drug Treated/Control)×100. For determination of oral activity, spontaneously breathing animals are pretreated orally for 2 hours (at 100 mg/kg) prior to challenge with leukotriene E.

7-[3-(4-Acetyl-3-hydroxy-2-propylphenoxy)-2-hydroxypropoxy]-4-oxo-8-propyl-4H-1-benzopyran-2-carboxylic acid (FPL 55712) elicits a 98% inhibition at 10 mg/kg, i.v., but is orally inactive in this test.

When N-[4-(1H-imidazol-1-yl)butyl]-2-(1-methylethyl)-11-oxo-11H-pyrido[2,1-b]quinazoline-8-carboxamide was utilized as the test substance, an $ID_{50}$ of 47 mg/kg, orally, and an $ID_{50}$ of 0.9 mg/kg, i.v. were obtained.

When 2-(1-methylethyl)-N-[4-(3-pyridyl)butyl]-11-oxo-11H-pyrido[2,1-b]quinazoline-8-carboxamide was utilized as the test substance, an $ID_{50}$ of 60 mg/kg, orally, and an $ID_{50}$ of 0.3 mg/kg, i.v. were obtained.

When 2-(1-methylethyl)-N-[4-[4-pyridyl]butyl]-11-oxo-11H-pyrido[2,1-b]quinazoline-8-carboxamide was utilized as the test substance, an $ID_{50}$ of 57 mg/kg, orally, and an $ID_{50}$ of 1.9 mg/kg/, i.v. were obtained.

(c) Guinea Pig Bronchoconstriction, In Vivo (Aerosol):

Male guinea pigs (Hartly strain) weighing 300 to 500 g are anesthetized with urethane (2 g/kg) intraperitoneally and a polyethylene cannula is inserted into the jugular vein for drug administration. Tracheal pressure is recorded from a cannula inserted in the trachea and connected to a Statham pressure transducer. After surgical preparation of the animals, a period of time is allowed for pulmonary functions to stabilize. The test compound is administered according to the following protocol. Propranolol (0.1 mg/kg) is administered intravenously while the animals breathed spontaneously. Five minutes thereafter, the animals are exposed for a five minute period to a 1% (w/v) aerosol solution of test compound (adjusted to an alkaline pH where necessary for drug solubilization) or to distilled water of the appropriate pH (for control purposes). A Monaghan (Model 750) ultrasonic nebulizer is used to administer all test compounds by inhalation. The nebulizer ultrasonic frequency is adjusted to produce particles in the 1–8$\mu$ diameter range (average 3$\mu$). Aqueous solutions are prepared fresh and introduced into the chamber of the nebulizer. The output of the nebulizer is made available to the animal by directing a bias flow of aerosol through a y tube connected to the tracheal cannula. At the end of the exposure period, the animals are paralyzed with succinylcholine (1.2 mg/kg, i.v.) and mechanically respirated (Harvard rodent respirator) at 40 breaths/minute and 2.5 cc tidal volume. Animals are then challenged with a maximum constrictory dose of leukotriene E delivered intravenously 30 seconds after administration of the succinylcholine.

The change (cm $H_2O$) between pre and peak ventilatory pressure readings is averaged for three control animals and five drug treated animals. The percent inhibition is calculated from the following formula:

(Control-Drug Tested/Control)×100

When various drug concentrations are tested, the percent inhibition at each concentration is plotted as log concentration (abscissa) versus percent inhibition (ordinate) and the $IC_{50}$ is determined from linear regression analysis.

In order to determine the aerosol half-life (t ½), the animals are prepared as described above, except that the time between aerosol exposure and challenge with leukotriene E is varied. All compounds are administered at the concentration necessary to inhibit leukotriene-induced bronchoconstriction by 80%. Biological half-life is calculated from plots of time (abscissa) versus log percent inhibition (ordinate).

Test results obtained when compounds of the invention were utilized in the foregoing test, are set out in Table I.

TABLE I

| Test Compound | ID$_{50}$ (% aerosol) | Biological half-life (min)[1] |
|---|---|---|
| N—[4-(1H—imidazol-1-yl)butyl]-2-(1-methylethyl)-11-oxo-11H—pyrido[2,1-b]quinazoline-8-carboxamide | 0.25 | 56 |
| 2-(1-methylethyl)-N—[4-(3-pyridyl)butyl]11-oxo-11H—pyrido[2,1-b]quinazoline-8-carboxamide | 0.30 | 7 |
| Isoproterenol | 0.00014 | 19.4 |
| PGE$_2$ | 0.00011 | 2.1 |
| 7-[3-(4-acetyl-3-hydroxy-2-propylphenoxy)-2-hydroxypropoxy]-4-oxo-8-propyl-4H—1-benzopyran-2-carboxylic acid (FPL 55712) | 0.75 | 77 |

(d) Assay for Thromboxane Synthase (TXA$_2$Syn.) Inhibitory Activity

TXA$_2$ syn. activity is measured by following the conversion of $^{14}$C-prostaglandin endoperoxide (PGH$_2$) to $^{14}$C-thromboxane A$_2$ (TXA$_2$) using microsomal fractions from human platelets as enzyme source. In the aqueous incubation medium, the TXA$_2$ decomposes rapidly into TXB$_2$. The amount of TXA$_2$ syn. is adjusted so that under the conditions of the assay approximately 80-90% of the substrate, PGH$_2$, is converted to product in control tubes. To prepare $^{14}$C-PGH$_2$, $^{14}$C-AA (50–60 mCi/mmole; Rose Chem.) is incubated with sheep seminal vesicular gland microsomes for 1.5 min at 37° and then the $^{14}$C-PGH$_2$ is extracted with diethylether, purified on columns of Sephadex LH-20 or silicic acid, and stored in acetone at −70° C. Incubations are done as follows. Sufficient $^{14}$C-PGH$_2$ to yield a final substrate concentration of 10 μM (∼30,000 cpm) is added to the incubation tubes and then the acetone is removed under nitrogen. The tubes are placed in an ice bath and then 215 μl of ice cold phosphate buffered saline, 10 μl of ethanol (control) or of test drug in ethanol, and 25 μl of the microsomal suspension are added with mixing in that order as rapidly as possible. The tubes are incubated at 22° for 2 minutes, the reaction is stopped and then the radioactive products and the uncoverted PGH$_2$ are extracted and analyzed by thin layer chromatography. The amount of $^{14}$C-PGH$_2$ converted to products is used as analyzed by thin layered chromatography. The amount of $^{14}$C-PGH$_2$ converted to products was used as a measure of TXA$_2$ synthase activity. Inhibitors were tested initially at a final concentration of 100 μM.

(e) Antagonism of Acetylcholine-induced Constriction in Guinea Pig Ilea

Anticholinergic activity was determined on a segment of guinea pig ileum that was suspended in a 37° C. bath of oxygenated Tyrodes solution. At 4 minute intervals, the ileum was challenged with $5.0 \times 10^{-7}$M acetylcholine for sufficient time to produce a peak contraction and then washed with fresh Tyrodes solution. After the tissue response to acetylcholine had stablized, the ileum was pretreated with the standard anticholinergic, atropine sulfate, for 1 minute prior to rechallenge with acetylcholine, the contraction recorded and the tissue washed with Tyrodes solution. Increasing concentrations of atropine sulfate were then given until the acetylcholine response was maximally inhibited. The IC$_{50}$ for atropine was $1 \times 10^{-8}$M. THe IC$_{50}$'s for test drugs were determined by this same procedure.

(f) Antagonism of Histamine-induced Constriction in Guinea Pig Ilea

Antihistaminic activity was determined on a segment of guinea pig ileum that was suspended in a 37° C. bath of oxygenated Tyrodes solution. At 4 minute intervals, the ileum was challenged with $1 \times 10^{-7}$M histamine for sufficient time to produce a peak contraction and then washed with fresh Tyrodes solution. After the tissue response to histamine had stabilized, the ileum was pretreated with the standard antihistaminic compound, pyrilamine maleate, for 1 minute prior to rechallenge with histamine, the contraction recorded, and the tissue washed with Tyrodes solution. Increasing concentrations of pyrilamine maleate were then given until the histamine response was maximally inhibited. By the IC$_{50}$ for pyrilamine maleate in the test system was $1 \times 10^{-8}$M. IC$_{50}$'s for test drugs were determined by this same procedure.

(g) Antagonism of PAF and Histamine-induced Bronchoconstriction in Guinea Pig

Spontaneously breathing male guinea pigs (Hartley strain) weighing 300–450 grams are dosed orally with test drug or control vehicle two hours prior to challenge with agonist. The animals are anesthetized with urethane (2 gm/kg) intraperitoneally and the jugular vein and trachea are cannulated. Two hours after dosing, the animal is paralyzed with succinylcholine (1.2 mg/kg, i.v.) and ventilated (Harvard rodent respirator) at 40 breaths/minutes and 2.5 cc tidal volume. Propranolol (0.1 mg/kg, i.v.) is administered and five minutes thereafter the animal is challenged with a constrictory dose of platelet activating factor (10 μg/kg, i.v.) or histamine dihydrochloride (20 μg/kg, i.v.). The change (cm H$_2$O) between pre and peak ventilatory pressure readings is averaged for three control animals and five drug treated animals. The percent inhibition is calculated from the following formula: (Control-Drug Treated/Control) × 100.

(h) Antagonism of KCl-induced Constriction in Guinea Pig Ilea

A 1–1.5 cm segment of guinea pig ileum removed from animals weighing 200–250 g is suspended in an organ bath containing 10 ml of Tyrodes solution with $10^{-6}$M atropine sulfate and $10^{-6}$M pyrilamine maleate. The bath is maintained at 37° C. and aerated with a mixture of 95% O$_2$ and 5% CO$_2$. KCl induces isometric constrictions of the ileum at concentrations between 10–30mM. The contractions consist of two phases, an initial fast contraction (the phasic portion), followed by a relaxation down to less intense but more prolonged contraction (the tonic phase). Varying concentrations of test drugs are incubated with the ileum for three minutes prior to KCl-challenge. The drug concentrations, which inhibit by 50% the phasic and tonic portion of the KCl-induced constrictions, are determined (IC$_{50}$'s).

(i) Inhibition of Cutaneous Anaphylaxis in Passively Sensitized Rats (l) Preparation of Antiserum IgE-containing rat antiserum (reaginic antiserum) was prepared according to the following procedure. Normal, male Sprague-Dawley rats (150–200 g) obtained from Charles River Laboratories, Wilmington, Mass., were immunized by an intraperitoneal injection of 0.5 ml Bordetella pertussis vaccine (Cannaught Laboratories, Willowdale, Toronto, Canada, 20 ou/ml) containing 100 μg egg albumin (Nutritional Biochemical Corp., Cleveland, Ohio). On day 16, *Nippostrongylus brasiliensis* (3000 larvae/0.1 ml) was administered subcutaneously and on day 21, 10 μg of egg albumin was administered intraperitoneally in 0.5 ml normal saline. On day 30, blood was collected by heart puncture and the serum was separated by centrifugation and refrigerated overnight at 5° C. The serum was assayed for antibody activity using the passive cutaneous anaphylaxis test after a 24 hour sensitization period (see below). Only those sera were used for the PCA test which produced an average wheal diameter of 3 mm or greater following an intradermal injection of 0.05 ml of a 1:50 dilution of serum in normal saline. These sera were pooled, divided into aliquots and kept frozen until used. The reaginic nature of the antiserum was demonstrated by the inactivation observed after heating for 4 hours at 56° C. This was further confirmed by incubating the serum in vitro with rat anti-IgE, anti-IgG, anti-IgA and anti-IgM. After incubating these samples for 1 hour at 20° C. and 16 hours at 4° C., they were centrifuged and the supernatants assayed for activity in the PCA test. Only the supernatants from incubations containing anti-IgE were inactive.

(2) Animal Procedure

The passive cutaneous anaphylaxis (PCA) test was performed on 190–220 g male Sprague-Dawley rats (Charles River Breeding Laboratories, Wilmington, Mass.), in a manner similar to that described by J. Goose and A.M.J.N. Blair, Immunology, 16, 749(1969). A 1:512 dilution of serum into saline was prepared and two aliquots (0.05 ml) of this titer of serum were injected intraderamally into the shaved skin of an animal's back (this amount of antibody produced a mean wheal diameter of approximately 7 mm). After a 24 hour sensitization period, 1 ml of an aqueous solution of 8 mg of egg albumin (National Biochemicals Corp., Cleveland, Ohio) and 5 mg of Evans Blue Dye (Nepera Chemical Co., Inc., Harriman, N.Y.) was administered intravenously via the tail vein to each rat. Forty minutes later, the animal was sacrificed by cervical dislocation and the dorsal skin removed for examination. The long and short axis of each wheal was measured with a metric vernier caliper and the average diameter was obtained for each reaction. Test compounds were either administered intravenously at the same time as antigen or orally at pretreatment times of 5, 10, 20, 30 or 60 minutes. For intravenous administration, the drugs were dissolved in dimethylsulfoxide (DMSO) at appropriate concentrations such that 0.1 ml of the DMSO solution could be administered per 100 g of animal body weight. For oral administration, the drugs were prepared in aqueous suspending vehicle (0.15M NaCl, containing 0.5 percent carboxymethyl cellulose; 0.4 percent Tween 80 and 0.9 percent benzyl alcohol) at appropriate concentrations such that 0.5 ml of the suspension could be administered per 100 g of body weight. For determination of oral $ID_{50}$'s, logarithmically spaced drug doses were administered at the time of peak activity. The procedure was conducted on 5 animals in the control and each of the treatment groups. Statistical analysis of the test results were conducted by the Student "t" test. The $ID_{50}$ was calculated by the method of J. Berkson, J.Am.Stat.Assoc., 48, 565(1953).

(j) In vitro SRS-A Antagonism

SRS-A was determined by bioassay on the guinea pig ileum using a modification of the method described by Orange et al., Adv. Immunol., 1969, 10, 105. A 1.5 cm segment of the ileum, obtained from male guinea pigs (175–200 g), was suspended in an organ bath containing Tyrodes solution with $10^{-6}M$ atropine sulfate and $10^{-6}M$ pyrilamine maleate. The bath was maintained at 37° C. and gassed with a mixture of 95 percent oxygen and 5 percent carbon dioxide. The ileum was attached to a strain gauge transducer and isotonic contractions recorded by a strip chart recorder. A resting tension of 0.5 g was applied and the tissue allowed to equilibrate for 1 hour.

The SRS-A used in these studies was obtained by challenging a large quantity of chopped lung fragments from actively sensitized guinea pigs with egg albumin in vitro. The animals were sensitized to egg albumin by an intraperitoneal injection of the antigen (1 ml of 10 mg/ml) in saline 28 to 45 days prior to challenge. The in vitro challenge was carried out by first preincubating the lung tissue (40 mg/ml) at 37° C. in Tyrodes solution for 5 minutes, adding the egg albumin (40 g/ml final concentration) to the fragments and after a 10 minute challenge, separating the media containing the SRS-A from the lung tissue by filtration on Whatman #1 filter paper. The concentration of SRS-A in the filtrate was calibrated by comparison of the contraction amplitude elicited in the bioassay system by a given volume of the supernatant with contractions obtained by varying concentrations of histamine. One unit of SRS-A is equivalent to that quantity which will give the same contraction as 5 ng of histamine. After standarization, the SRS-A was stored in small aliquots at $-80°$ C. for further use. Contractions elicited by SRS-A were allowed to proceed for 5 minutes before washing the tissue with Tyrodes solution. SRS-A antagonism was determined by pretreating the ileum with drug for 30 seconds prior to the addition of a concentration of SRS-A which have a submaximal response, determination of the amplitude of contraction elicited in the presence of drug and then washing the ileum with Tyrodes. In this same system, the $IC_{50}$ for the reference inhibitor compound 7-[3-(4-acetyl-3-hydroxy-2-propylphenoxy)-2-hydroxypropoxy]-4-oxo-8-propyl-4H-1-benzopyran-2-carboxylic acid (FPL 55712) was $3 \times 10^{-8}M$.

Test results obtained when compounds of the invention were utilized in test procedures (d–j) are set out in Table II.

TABLE II

| Test Procedure (d–j) | Compound A[1] | $IC_{50}$ ($ID_{50}$) Compound B[2] | Compound C[3] |
|---|---|---|---|
| (d) $TXA_2$ synthase in human platelet microsomes | $10^{-7}$ to $10^{-6}$ M | $10^{-7}$–$10^{-6}$ M | $10^{-7}$ M |
| (e) Antagonism of acetylcholine-induced constrictions in guinea pig ilea | $5 \times 10^{-6}$ M | $7 \times 10^{-6}$ | — |
| (f) Antagonism of histamine-induced constriction in guinea pig ilea | $1 \times 10^{-6}$ M | $2 \times 10^{-6}$ M | — |
| (g) Antagonism of PAF-induced bronchoconstriction in the guinea pig | 13 mg/kg (p.o., 2 hour pretreatment) | 100 mg/kg | 50 mg/kg |

TABLE II-continued

| Test Procedure (d–j) | Compound A[1] | IC$_{50}$ (ID$_{50}$)<br>Compound B[2] | Compound C[3] |
|---|---|---|---|
| (g) Antagonism of histamine-induced bronchoconstriction in guinea pigs | 39 mg/kg (p.o., 2 hour pretreatment) | — | — |
| (h) Antagonism of KCl-induced constriction in guinea pig ilea | 1.7 × 10$^{-5}$ M (phasic)<br>1 × 10$^{-5}$ M (tonic) | 1.3 × 10$^{-5}$ M (phasic)<br>8 × 10$^{-6}$ M (tonic) | 5.4 × 10$^{-6}$ (phasic)<br>2.4 × 10$^{-6}$ (tonic) |
| (i) Inhibition of allergic mediator release in the rat passive cutaneous anaphylaxis test | 20 mg/kg (p.o., 10 minute pretreatment) | 21 mg/kg (p.o., 5 minute pretreatment) | — |
| (j) In vitro SRS—A Antagonism | 1 × 10$^{-6}$ M | 1 × 10$^{-6}$ M | |

[1]Compound A — N—[4-(1H—imidazol-1-yl)butyl]-2-(1-methylethyl)-11-oxo-11H—pyrido[2,1-b]quinazoline-8-carboxamide.
[2]Compound B — 2-(1-methylethyl)-N—[4-(3-pyridyl)butyl]-11-oxo-11H—pyrido[2,1-b]quinazoline-8-carboxamide.
[3]Compound C — 2-(1-methylethyl)-N—[6-(3-pyridyl)hexyl]-11-oxo-11H—pyrido[2,1-b]quinazoline-8-carboxamide.

(k) Prevention of Mortality Induced by Platelet Aggregating Factor (PAF)

Male CF$_1$ mice weighing 20–30 gms (Carworth Farms Co.) are fed ad libitum. Racemic 2-[[[2-(acetyloxy)-3-(octadecyloxy)propoxy]hydroxyphosphinyl]oxy]-N,N,N-trimethylethanaminium hydroxide inner salt hemihydrate (PAF) is concentrated in ethanol at a concentration of 1 mg/ml. At the time of experimentation, PAF is diluted in 0.1% BSA (bovine serum albumin) and administered intravenously at a dose of 0.10 mg/kg one hour after 10 mice are dosed with either vehicle (BSA) or drug. Mortality in mice treated with PAF occurs within 30 minutes after i.v. administration. Mortality in mice of at least 80% was achieved with PAF alone.

When 2-(1-methylethyl)-N-[6-(3-pyridyl)hexyl]-11-oxo-11H-pyrido[2,1-b]quinzoline-8-carboxamide was used as a test substance, it prevented PAF induced mortality. A calculated oral ID$_{50}$ (Inhibiting Dose) of 13 mg/kg was obtained with this compound.

When 2-(1-methylethyl)-N-[6-(1H-imidazol-1-yl)hexyl]-11-oxo-11H-pyrido[2,1-b]quinazoline-8-carboxamide was used as the test substance, an oral ID$_{50}$ of 17 mg/kg was obtained.

(l) Assay for Platelet Aggregation In Vitro

The turbidometric method of G. V. R. Born, Nature 194, 927 (1962) is used. Platelet rich plasma (PRP) and platelet poor plasma (PPP) are prepared with 0.38% sodium citrate-treated blood. Speed and time of centrifugation varied with different species; human:160 g for 20 minutes, dog:160 g for 15 minutes, guinea pig and rabbit:160 g for 15 minutes, and rat:230 g for 10 minutes. Aggregation is monitored with a Payton dual channel module or Chronolog lumiaggregometer when the release of ATP is simultaneously measured. 0.45 ml of PRP is added to a cuvette and prewarmed to 37° C. The stimulant (arachidonic acid or synthetic platelet activating factor) is added in volumes of 50 μl; all other agents in 5 μl. Vehicles are added to samples not containing agents. 0 to 100% light transmission is set with PRP and PPP. % aggregation is calculated from the % increase in light transmission at 5 minutes after the addition of the aggregating agent. For inhibition of aggregation studies the inhibitor is added first and preincubated with the platelets for 1 minute with stirring, followed by the stimulant. % inhibition is calculated from the % aggregation with and without the test compound.

$$\% \text{ inhibition} = \frac{(\% \text{ aggregation } + \text{ compound})}{(1 - \% \text{ aggregation } + \text{ vehicle})} \times 100$$

Test results obtained when compounds of the invention were utilized in this test procedure are set out in Table III.

TABLE III
Inhibitors of Arachidonic Acid and Platelet Activating Factor[1] Induced Platelet Aggregation

| R | X | N | Het | AA[2] | PAF[2] |
|---|---|---|---|---|---|
| (CH$_3$)$_2$CH | NH | 4 | 3-pyridyl | + | + |
| HO | NH | 4 | 3-pyridyl | + | + |
| CH$_3$ | NH | 4 | 3-pyridyl | + | — |
| (CH$_3$)$_2$CH—O | NH | 4 | 3-pyridyl | + | + |
| (CH$_3$)$_2$CH | NH | 6 | 3-pyridyl | + | + |
| (CH$_3$)$_2$CH | NH | 4 | 4-pyridyl | — | + |
| (CH$_3$)$_2$CH | NH | 5 | 4-pyridyl | + | + |
| (CH$_3$)$_2$CH | —O— | 3 | 3-pyridyl | — | + |
| (CH$_3$)$_2$CH | NH | 2 | 4-thiopyridyl | + | + |
| (CH$_3$)$_2$CH | NH | 4 | 1-imidazol | + | — |
| (CH$_3$)$_2$CH | NH | 5 | 1-imidazol | + | — |

[1]Platelet Activating Factor is racemic 2-[[[2-(acetyloxy)-3-(octadecyloxy)propoxy] hydroxyphosphinyl]oxy]-N,N,N—trimethylethanaminium hydroxide inner salt hemihydrate.
[2]IC$_{50}$ < 10 μM are designated by (+).

(m) PAF Radioreceptor Binding Assay

Platelet rich plasma is prepared by centrifugation of citrate-treated dog blood. Acidification to pH 6.5 with 0.15M citric acid and centrifugation for 10 minutes at 1000 g yields a platelet pellet which is then washed by resuspension in EDTA-Phosphate Buffered Saline (PBS) and recentrifuged. The washed platelet preparation is adjusted to 2 × 10$^7$ platelets/50 μl in 0.1% BSA-PBS.

To a 400 l microfuge tube containing 50 μl silicone oil (specific gravity 1.023) is added buffer, PAF standard or analog, or an extract to bring the aqueous volume to 150 μl. 50 μl of $^3$H-PAF (10,000 cpm, 45 Ci/mM) is added followed by 2 × 10$^7$ dog platelets. After mixing, incubating for 10 minutes at room temperature, and centrifuging for 1 minute in a Beckman Microfuge B (8000 g), the pellet is removed by clipping off the tip of the tube, solubilizing the platelets with 200 μl of 50% methanol, and counting in 10 ml of Aquasol. A curve of 50–2500 pg/tube is obtained within 10 minutes of incubation which demonstrates high specificity and correlation with biological activity for PAF and its analogs.

When 2-(1-methylethyl)-N-[4-(3-pyridinyl)butyl]-11-oxo-11H-pyrido[2,1-b]quinazoline-8-carboxamide was used as the test substance, an IC$_{50}$ of 0.45 (μM) was obtained.

When 2-(1-methylethyl)-N-[6-(3-pyridinyl)hexyl]-11-oxo-11H-pyrido[2,1-b]quinazoline-8-carboxamide was used as the test substance, an IC$_{50}$ of 1.0 (μM) was obtained.

In the practice of the invention, the dose of a compound of formula I or formula II, or a salt thereof, to be administered and the frequency of administration will be dependent on the potency and duration of activity of the particular compound of formula I or formula II, or a salt thereof, to be administered and on the route of administration, as well as the severity of the conditions, age of the mammal to be treated and the like. Doses of a compound of formula I or formula II, or a salt thereof, contemplated for use in practicing the invention are in the range of from about 100 to about 1500 mg per day, either as a single dose or in divided doses.

A compound of formula I or formula II, or a salt thereof, or a composition containing a therapeutically effective amount of a compound of formula I or formula II, or a salt thereof, can be administered by methods well known in the art. Thus, a compound of formula I or formula II, or a salt thereof, can be administered either singly or with other pharmaceutical agents, for example, antihistamines, mediator release inhibitors, methyl xanthines, $beta_2$ agonists or antiasthmatic steroids such as prednisone and predinisolone, orally, parenterally, rectally or by inhalation, for example, in the form of an aerosol, micropulverized powder or nebulized solution. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or water or combinatitons of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the aerosol composition.

The Examples which follow further illustrate the invention. All parts are by weight and all temperatures are in degrees centigrade, unless otherwise mentioned.

EXAMPLE 1

Preparation of
2-(1-methylethyl)-11-oxo-11H-pyrido[2,1-b]quinazoline-8-carboxylic acid 3-(3-pyridine)propyl ester (Method A)

A mixture of 5.0 g of 2-(1-methylethyl)-11-oxo-11H-pyrido[2,1-b]quinazoline-8-carboxylic acid, 5.2 g of 3-(3-pyridine)propylbromide hydrobromide, and 5.2 g of potassium carbonate in 200 ml of dimethylformamide was heated to a bath temperature of 70° C. for 45 minutes. The reaction mixture was partitioned between water (100 ml) and dichloromethane (100 ml) and the aqueous layer was extracted with 3×100 ml of dichloromethane. The combined extracts were washed with 100 ml portions of 10% sodium hydroxide and water, were dried over potassium carbonate and evaporated to 6.3 g of an oil which was purified by preparative liquid chromatography over silica gel eluting with 3:1 ethyl acetate-hexane. The major fraction contained 4.6 g of a orange oil which was crystallized from ethyl acetate-hexane to give 2.7 g (38%) of 2-(1-methylethyl)-11-oxo-11H-pyrido[2,1-b]quinazoline-8-carboxylic acid 3-(3-pyridyl)propyl ester, mp 108°–109° C.

The hydrochloride salt was obtained from aqueous isopropanol-ether and melted 226°–227° C.

EXAMPLE 2

Preparation of
N-[2-(3-pyridyl)ethyl]-2-(1-methylethyl)-11-oxo-11H-pyrido[2,1-b]quinazoline-8-carboxamide (Method B)

A mixture of 20.84 g of 2-(1-methylethyl)-11-oxo-11H-pyrido[2,1-b]quinazoline-8-carboxylic acid in 400 ml of thionyl chloride was heated to reflux until complete solution occurred. The thionyl chloride was removed under reduced pressure and the residue was diluted with 4×100 ml of toluene and evaporated. The residue was dissolved in toluene and treated with 9.00 g of 2-(3-pyridyl)-ethanamine and the solution was heated to reflux for 6 hours. The resulting mixture was concentrated and the residue was partitioned between dichloromethane and water. The organic phase was dried over magnesium sulfate, evaporated, and the residue was made acidic with hydrochloric acid. Crystallization from ethanol gave 11.5 g of N-[2-(3-pyridyl)ethyl]-2-(1-methylethyl)-11-oxo-11H-pyrido[2,1-b]-quinazoline-8-carboxamide, mp 283°–292° C. Three recrystallizations from ethanol-ether yielded 2.75 g (8%), mp 293°–296° C.

EXAMPLE 3

Preparation of
N-[6-(3-pyridyl)hexyl]-2-(1-methylethyl)-11-oxo-11H-pyrido[2,1-b]quinazoline-8-carboxamide (Method C)

To an ice-cold suspension of 16.15 g of 2-(1-methylethyl)-11-oxo-11H-pyrido[2,1-b]quinazoline-8-carboxylic acid, 15.75 g of diphenylphosphorylazide, and 10.2 g of 6-(3-pyridyl)-hexanamine in 100 ml of dry dimethylformamide was added 8.0 ml of triethylamine. The reaction mixture was held at 0° C. for 2 hours and allowed to warm to room temperature over night. The resulting clear, yellow solution was diluted with water and 5M sodium hydroxide solution and was extracted with 3×300 ml of dichloromethane. The combined organic layers were dried over potassium carbonate and evaporated to a yellow semi-solid which was recrystallized from ethyl acetate-hexane to give 21.22 g (84%) of N-[6-(3-pyridyl)hexyl]-2-(1-methylethyl)-11-oxo-pyrido[2,1-b]-quinazoline-8-carboxamide, mp 94°–96° C. Recrystallization gave mp 100°–103° C. Conversion to the dihydrochloride salt gave 22.12 g, mp 230°–236° C. (dec.) and recrystallization from ethanol-ether gave 21.06 g, mp 234°–240° C. (dec.).

EXAMPLE 4

Preparation of
N-[4-(1H-imidazol-1-yl)butyl]-2-(1-methylethyl)-11-oxo-11H-pyrido[2,1-b]quinazoline-8-carboxamide (Method D)

A solution of 1.30 g of cyanomethyl 2-(1-methylethyl)-11-oxo-11H-pyrido[2,1-b]quinazoline-8-carboxylate and 1.20 g of (1H-imidazol-1-yl)butanamine in 15 ml of dimethylformamide was stirred at a bath temperature of 35° C. for 18 hours. The reaction mixture was diluted with water and the crude precipitate was recrystallized from acetonitrile to give 1.41 g (85%) of N-[4-(1H-imidazol-1-yl)butyl]-2-(1-methylethyl)-11-oxo-11H-pyrido[2,1-b]quinazoline-8-carboxamide, mp 165°–167° C.

Examples 5-48
Pyrido[2,1-b]quinazoline-8-carboxylic Acid Derivatives of Formula I(c) prepared by the method described in Example 1, 2, 3 or 4.

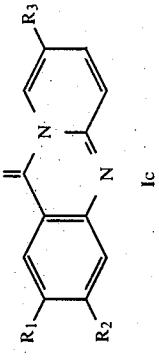

I$_c$

| Example | R$_1$ | R$_2$ | R$_3$ | Method | Yield % | mp °C. | Recryst. Solvent | Formula |
|---|---|---|---|---|---|---|---|---|
| 5 | (CH$_3$)$_2$CH— | H | —C(=O)—NH—(CH$_2$)$_3$—(3-pyridyl) | C | 52 | 221-222 | EtOH—Et$_2$O | C$_{24}$H$_{24}$N$_4$O$_2$.2HCl.H$_2$O |
| 6 | (CH$_3$)$_2$CH— | H | —C(=O)—NH—(CH$_2$)$_4$—(3-pyridyl) | C | 48 | 247-252 | EtOH—Et$_2$O | C$_{25}$H$_{26}$N$_4$O$_2$.2HCl |
| 7 | (CH$_3$)$_2$CH— | H | —C(=O)—NH—(CH$_2$)$_5$—(3-pyridyl) | C | 60 | 227-230 | EtOH—Et$_2$O | C$_{26}$H$_{28}$N$_4$O$_2$.2HCl |
| 8 | (CH$_3$)$_2$CH— | H | —C(=O)—N(CH$_3$)—(CH$_2$)$_4$—(3-pyridyl) | C | 65 | 216-218 | EtOH—Et$_2$O | C$_{26}$H$_{28}$N$_4$O$_2$.2HCl |
| 9 | (CH$_3$)$_2$CH— | H | —C(=O)—NH—(CH$_2$)$_4$O—(3-pyridyl) | C | 65 | 200-204 | PrOH—Et$_2$O | C$_{25}$H$_{26}$N$_4$O$_3$.2HCl.H$_2$O |
| 10 | (CH$_3$)$_2$CH— | H | —C(=O)—NH—(CH$_2$)$_4$—(4-pyridyl) | C | 50 | 259-261 | EtOH | C$_{25}$H$_{26}$N$_4$O$_2$.2HCl |

-continued
Examples 5-48
Pyrido [2,1-b] quinazoline-8-carboxylic Acid Derivatives of Formula I(c) prepared by the method described in Example 1, 2, 3 or 4.

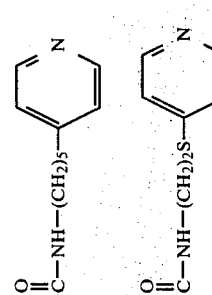

Ic

| Example | $R_1$ | $R_2$ | $R_3$ | Method | Yield % | mp °C. | Recryst. Solvent | Formula |
|---|---|---|---|---|---|---|---|---|
| 11 | $(CH_3)_2CH-$ | H | $-\overset{O}{\underset{\|}{C}}-NH-(CH_2)_5-\!\!\left\langle\!\!\begin{array}{c}N\\ \end{array}\!\!\right\rangle$ | C | 38 | 158–159 | $CH_2Cl_2$—Hex | $C_{26}H_{28}N_4O_2$ |
| 12 | $(CH_3)_2CH-$ | H | $-\overset{O}{\underset{\|}{C}}-NH-(CH_2)S-\!\!\left\langle\!\!\begin{array}{c}N\\ \end{array}\!\!\right\rangle$ | C | 68 | 156–159, 190 | $CH_2Cl_2$—Hex | $C_{23}H_{22}N_4O_2S$ |
| 13 | $(CH_3)_2CH-$ | H | $-\overset{O}{\underset{\|}{C}}-NH-(CH_2)_4S-\!\!\left\langle\!\!\begin{array}{c}N\\ \end{array}\!\!\right\rangle$ | C | 55 | 169–171 | $CH_2Cl_2$—Hex | $C_{25}H_{26}N_4O_2S$ |
| 14 | $(CH_3)_2CH-$ | H | $-\overset{O}{\underset{\|}{C}}-NH-(CH_2)_3-N\!\!\left[\!\!\begin{array}{c}N\\ \end{array}\!\!\right]$ | C | 47 | 265–267 | EtOH | $C_{22}H_{23}N_5O_2\cdot 2HCl\cdot 0.58H_2O$ |
| 15 | $(CH_3)_2CH-$ | H | $-\overset{O}{\underset{\|}{C}}-NH-(CH_2)_4-N\!\!\left[\!\!\begin{array}{c}N\\ \end{array}\!\!\right]$ | C | 42 | 261–263 | EtOH—$Et_2O$ | $C_{23}H_{25}N_5O_2\cdot 2HCl$ |
| 16 | $(CH_3)_2CH-$ | H | $-\overset{O}{\underset{\|}{C}}-NH-(CH_2)_5-N\!\!\left[\!\!\begin{array}{c}N\\ \end{array}\!\!\right]$ | C | 13 | 232–234 | EtOH | $C_{24}H_{27}N_5O_2\cdot 2HCl$ |
| 17 | $CH_3-$ | H | $-\overset{O}{\underset{\|}{C}}-NH-(CH_2)_4-\!\!\left\langle\!\!\begin{array}{c}N\\ \end{array}\!\!\right\rangle$ | C | 66 | 289–290 | EtOH—$Et_2O$ | $C_{23}H_{22}N_4O_2\cdot 2HCl$ |

Examples 5-48
Pyrido [2,1-b] quinazoline-8-carboxylic Acid Derivatives of Formula I(c) prepared by the method described in Example 1, 2, 3 or 4.

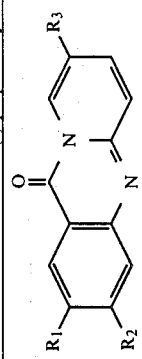

Ic

| Example | $R_1$ | $R_2$ | $R_3$ | Method | Yield % | mp °C. | Recryst. Solvent | Formula |
|---|---|---|---|---|---|---|---|---|
| 18 | $CH_3O-$ | H | $-\overset{O}{\underset{\|}{C}}-NH-(CH_2)_4-$ pyridyl | C | 75 | 172-173 | THF—Hex | $C_{23}H_{22}N_4O_3$ |
| 19 | $(CH_3)_2CHO-$ | H | $-\overset{O}{\underset{\|}{C}}-NH-(CH_2)_4-$ pyridyl | C | 81 | 253-255 | EtOH—Et$_2$O | $C_{25}H_{26}N_4O_3.2HCl.0.66H_2O$ |
| 20 | H | H | $-\overset{O}{\underset{\|}{C}}-NH-(CH_2)_4-$ pyridyl | C | 53 | 179-183 | iProh—CH$_2$Cl$_2$—Hex | $C_{22}H_{20}N_4O_2$ |
| 21 | Br— | H | $-\overset{O}{\underset{\|}{C}}-NH-(CH_2)_4-$ pyridyl | C | 50 | 197-199 | CH$_2$Cl$_2$—CH$_3$CN | $C_{22}H_{19}BrN_4O_2$ |
| 22 | HO— | H | $-\overset{O}{\underset{\|}{C}}-NH-(CH_2)_4-$ pyridyl | C | 11 | 244 | DMF—H$_2$O | $C_{22}H_{20}N_4O_2.\frac{3}{2}H_2O$ |
| 23 | H | $CH_3O-$ | $-\overset{O}{\underset{\|}{C}}-NH-(CH_2)_4-$ pyridyl | C | 48 | 184-186 | CH$_2$Cl$_2$—CH$_3$CN | $C_{23}H_{22}N_4O_3$ |

-continued
Examples 5-48
Pyrido [2,1-b] quinazoline-8-carboxylic Acid Derivatives of Formula I(c) prepared by the method described in Example 1, 2, 3 or 4.

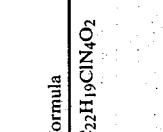

Ic

| Example | $R_1$ | $R_2$ | $R_3$ | Method | Yield % | mp °C. | Recryst. Solvent | Formula |
|---------|-------|-------|-------|--------|---------|--------|------------------|---------|
| 24 | H | Cl— |  —C(=O)—NH—(CH$_2$)$_4$— [3-pyridyl] | C | 23 | 175-178 | CH$_2$Cl$_2$—CH$_3$CN | C$_{22}$H$_{19}$ClN$_4$O$_2$ |
| 25 | CH$_3$— | CH$_3$— | —C(=O)—NH—(CH$_2$)$_4$— [3-pyridyl] | C | 53 | 188-189.5 | CH$_2$Cl$_2$—CH$_3$CN | C$_{24}$H$_{24}$N$_4$O$_2$ |
| 26 | (CH$_3$)$_2$CH— | H | —C(=O)—NH—(CH$_2$)$_2$— [2-pyridyl] | B | 35 | 248-250 | CH$_3$OH—Et$_2$O | C$_{23}$H$_{22}$N$_4$O$_2$·2HCl |
| 27 | (CH$_3$)$_2$CH— | H | —C(=O)—NH—(CH$_2$)$_4$— [2-pyridyl] | C | 49 | 118-120 | EtOAc—Hex | C$_{25}$H$_{26}$N$_4$O$_2$ |
| 28 | (CH$_3$)$_2$CH— | H | —C(=O)—NH—(CH$_2$)$_2$SCH$_2$— [3-pyridyl] | C | 36 | 204-210 | aq.EtOH—Et$_2$O | C$_{24}$H$_{24}$N$_4$O$_2$·2HCl |
| 29 | (CH$_3$)$_2$CH— | H | —C(=O)—NH—(CH$_2$)$_7$— [3-pyridyl] | C | 75 | 103-105 | EtOAc—Hex | C$_{28}$H$_{32}$N$_4$O$_2$ |

-continued
Examples 5-48
Pyrido [2,1-b] quinazoline-8-carboxylic Acid Derivatives of Formula I(c) prepared by the method described in Example 1, 2, 3 or 4.

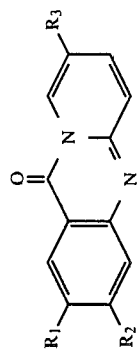

| Example | $R_1$ | $R_2$ | $R_3$ | Method | Yield % | mp °C. | Recryst. Solvent | Formula |
|---|---|---|---|---|---|---|---|---|
| 30 | $(CH_3)_2CH-$ | H | $-C(O)-NH-(CH_2)_2SCH_2-$(4-pyridyl) | C | 53 | 140-142 | EtOAc | $C_{24}H_{24}N_4O_2S$ |
| 31 | $(CH_3)_2CH-$ | H | $-C(O)-NH-(CH_2)_6-N$(imidazole) | C | 48 | 135-136 | EtOAc | $C_{25}H_{29}N_5O_2$ |
| 32 | $(CH_3)_2CH-$ | H | $-C(O)-NH-(CH_2)_4-N$(2-methylimidazole) | C | 4 | 270-272 | $CH_3OH-CH_3CN$ | $C_{24}H_{27}N_5O_2.2HCl$ |
| 33 | $(CH_3)_2CH-$ | H | $-C(O)-NH-CH(CH_3)-(CH_2)_2-$(3-pyridyl) | C | 44 | 156-159 | $CH_3CN$ | $C_{25}H_{26}N_4O_2$ |
| 34 | $(CH_3)_2CH-$ | H | $-C(O)-NH-(CH_2)_4-$(pyrimidinyl) | D | 64 | 170-171 | $CH_3CN-CH_3OH$ | $C_{24}H_{25}N_5O_2$ |
| 35 | $(CH_3)_2CH-$ | H | $-C(O)-NH-(CH_2)_6-$(pyrimidinyl) | D | 63 | 132-134 | $CH_3CN$ | $C_{26}H_{29}N_5O_2$ |

-continued
Examples 5-48
Pyrido [2,1-b] quinazoline-8-carboxylic Acid Derivatives of Formula I(c) prepared by the method described in Example 1, 2, 3 or 4.

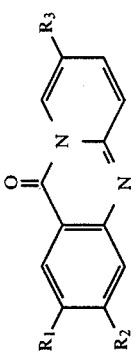

Ic

| Example | $R_1$ | $R_2$ | $R_3$ | Method | Yield % | mp °C. | Recryst. Solvent | Formula |
|---|---|---|---|---|---|---|---|---|
| 36 | $CH_3$— | $CH_3$— | —C(O)NH—(CH$_2$)$_4$—[pyrimidinyl] | B | 55 | 205-207 | CHCl$_3$ | $C_{23}H_{23}N_5O_2$ |
| 37 | $(CH_3)_2CH$— | H | —C(O)NHCH(CH$_2$)$_2$—[pyrimidinyl], CH$_3$ | C | 33 | 204-206 | EtOH—Et$_2$O | $C_{24}H_{25}N_5O_2$ |
| 38 | HO— | H | —C(O)NH(CH$_2$)$_6$—[pyridyl] | D | 43 | 211-212 | DMF | $C_{24}H_{24}N_4O_3$ |
| 39 | HO— | H | —C(O)NH(CH$_2$)$_4$—N[imidazolyl] | D | 58 | 320-322 | DMF | $C_{20}H_{19}N_5O_3$ |
| 40 | $(CH_3)_2CH$— | H | —C(O)N(CH$_2$)$_4$—N[imidazolyl], CH$_3$ | C | 32 | 202-204 | EtOH—Et$_2$O | $C_{24}H_{27}N_5O_2\cdot2HCl\cdot0.5H_2O$ |
| 41 | $(CH_3)_2CH$— | H | —C(O)NHCH(CH$_2$)$_3$—N[imidazolyl], CH$_3$ | C | 41 | 226-228 | MeOH—CH$_3$CN | $C_{24}H_{27}N_5O_2\cdot2HCl$ |
| 42 | $(CH_3)_2CH$— | H | —C(O)NCH(CH$_2$)$_3$—N[imidazolyl], CH$_3$ | C | 9 | 235-239 | MeOH—Et$_2$O | $C_{25}H_{29}N_5O_2\cdot2HCl$ |

-continued
Examples 5-48
Pyrido [2,1-b] quinazoline-8-carboxylic Acid Derivatives of Formula I(c) prepared by the method described in Example 1, 2, 3 or 4.

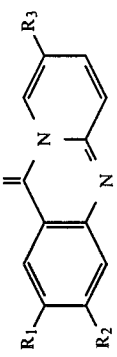

Ic

| Example | $R_1$ | $R_2$ | $R_3$ | Method | Yield % | mp °C. | Recryst. Solvent | Formula |
|---|---|---|---|---|---|---|---|---|
| 43 | $(CH_3)_2CH-$ | H | $-\overset{O}{\underset{}{C}}NHCH(CH_2)_3$—[3-pyridyl], with $CH_3$ branch | C | 21 | 95-96 | EtOAC—Hex | $C_{26}H_{28}N_4O_2$ |
| 44 | $(CH_3)_2CH-$ | H | $-\overset{O}{\underset{}{C}}NH(CH_2)_6$—[3-quinolinyl] | D | 71 | 140-141.5 | $CH_3CN$ | $C_{31}H_{32}N_4O_2$ |
| 45 | $(CH_3)_2CH-$ | H | $-\overset{O}{\underset{}{C}}NH(CH_2)_6$—[2-thienyl] | D | | | | $C_{26}H_{29}N_3O_2S$ |
| 46 | $CH_3-$ | $CH_3-$ | $-\overset{O}{\underset{}{C}}NH(CH_2)_3-\overset{\oplus}{N}$—pyridinium $Cl^\ominus$ | B | 58 | 253-257 dec. | EtOH | $C_{23}H_{23}ClN_4O_2 \cdot 0.5H_2O$ |
| 47 | $CH_3-$ | $CH_3-$ | $-\overset{O}{\underset{}{C}}NH(CH_2)_4-\overset{\oplus}{N}$—pyridinium $Cl^\ominus$ | B | 26 | 245-247 dec. | EtOH | $C_{24}H_{25}ClN_4O_2 \cdot 2H_2O \cdot 1.2HCl$ |
| 48 | $CH_3-$ | $CH_3-$ | $-\overset{O}{\underset{}{C}}NH(CH_2)_6$—[3-pyridyl] | B | 58 | 253-257 dec. | EtOH | $C_{26}H_{28}N_4O_2 \cdot 2HCl$ |

EXAMPLE 9

Preparation of
2-(1-methylethyl)-11-oxo-11H-pyrido[2,1-b]-quinazoline-8-carboxylic acid 4-(3-pyridinyl)butyl ester A suspension of 0.70 g of 2-(1-methylethyl)-11-oxo-11H-pyrido[2,1-b]quinazoline-8-carboxylic acid, 0.50 g of 4-(3-pyridinyl)butylchloride, 0.40 g of potassium iodide and 0.39 g of potassium carbonate in 12 ml of dimethylformamide was stirred over night at a bath temperature of 50° C. The reaction mixture was diluted with ethylacetate, washed with water, dried (potassium carbonate) and concentrated. The residue was chromatographed on 75 g of silica gel eluting with ethyl acetate to give 0.46 g of a yellow solid which was recrystallized from ethyl acetate-hexane to give 0.33 g (32%), mp 95°–96° C.

EXAMPLE 50

Preparation of
3-[4-[[(2,3-dimethyl-11-oxo-11H-pyrido[2,1-b]quinazolin-8-yl)carbonyl]amino]butyl]-1-methyl-pyridinium iodide A mixture of 2.2 g of 2,3-dimethyl-11-oxo-N-[4-(3-pyridinyl)butyl]-11H-pyrido[2,1-b]quinazoline-8-carboxamide and 10 ml of iodomethane was stirred at room temperature, under argon form 3 days. An orange gum was obtained after removal of the excess iodomethane which was crystallized from methanol to yield 2.3 g (77.2%) of orange crystals, m.p. 129° dec.

EXAMPLE 51

Preparation of
2-[3-(3-pyridyl)propyl]-1H-isoindole-1,3(2H)-dione

A total of 76.4 g of 3-(3-pyridyl)propyl bromide was partitioned between aqueous sodium hydroxide and 200 ml of ether. The ether layer was dried over potassium carbonate and diluted with 250 ml of dimethylformamide which contained 60.0 g of potassium phthalimide and the bath temperature was raised gradually as the ether distilled. The bath temperature was finally held at 130° C. over night, an additional 24.0 g of potassium phthalimide was added and heating was continued for 18 hours. The resulting mixture was partitioned between ether and water; the ether layer was dried over potassium carbonate and evaporated to give a solid which was crystallized from dichloromethane-hexane to give 22.0 g (30%) of 2-[3-(3-pyridyl)propyl]-1H-isoindole-1,3(2H)-dione, mp 88°–89° C. The analytical sample was obtained from dichloromethanehexane and melted 89°–91° C.

EXAMPLE 52

Preparation of 3-pyridinepropanamine

A mixture of 11.3 g of 2-[3-(3-pyridyl)propyl]-1H-isoindole-1,3(2H)-dione and 10.1 g of hydrazine hydrate was refluxed in 200 ml of ethanol for 6 hours, allowed to cool, and was filtered. The filtrate was concentrated and the residue distilled to give 4.77 g (70%) of 3-pyridinepropanamine, bp 84°–86° C./0.35 mm.

EXAMPLE 53

Preparation of 3-pyridinebutanenitrile

A stirred solution of 1040 g of 3-(3-pyridyl)propyl bromide hydrochloride in 1 L of ice and water was layered with 2 L of ether and was neutralized to pH 7 by the slow addition of 5M potassium hydroxide. The temperature was maintained at 0° C. during the neutralization by addition of ice in portions. The layers were separated and the aqueous phase was extracted with 2×2 L of ether and the combined ether layers were dried briefly over sodium sulfate and were concentrated under reduced pressure at a temperature of 30° C. to give 760 g of the free base of 3-(3-pyridyl)propyl bromide.

The crude product from above was dissolved in 3 L of ethanol and a solution of 361 g of potassium cyanide in 2 L of water was added all at once. The resulting mixture was heated to reflux for 8 hours, cooled, and concentrated to remove excess ethanol. The aqueous residue was saturated with sodium chloride and extracted with 4×1 L of dichloromethane. The combined extracts were washed with brine, dried over sodium sulfate and evaporated to give 385 g of a black oil. Distillation afforded 335 g (63%) of 3-pyridinebutanenitrile, bp 110°–115° C./0.3 mm.

EXAMPLE 54

Preparation of 3-pyridinebutanamine

3-Pyridinebutanamine was obtained by hydrogenation of 78.6 g of 3-pyridinebutanenitrile dissolved in 850 ml of methanol and 20 ml of triethylamine over 20 g of Raney cobalt at a hydrogen pressure of 1000 psi and at temperature of 100° C. for 2.5 hours. The residue obtained after filtration and concentration was distilled to give 69.8 g (86%) of 3-pyridinebutanamine, bp 118°–120° C./1 mm. The product was further characterized as the dihydrochloride salt which was crystallized from ethanol-ether, mp 133°–134° C.

EXAMPLE 55

Preparation of 3-pyridinevaleric acid

To a solution of sodium ethoxide prepared from 9.2 g of sodium in 200 ml of ethanol was added 32.0 g of diethyl malonate and 56.0 g of the hydrobromide salt of 3-(3-pyridyl)propyl bromide in 30 ml of ethanol. The resulting mixture was heated to reflux for 1 hour, was cooled and concentrated. The residue was triturated with ether and the ether was evaporated to give 53.2 g of crude product which was purified by preparative liquid chromatography over silica gel eluting with 1:1 ethyl acetate-hexane to give 36 g (65%) of a malonic ester. This material was dissolved in 200 ml of 20% hydrochloric acid and heated to reflux over night. The solvent was removed under reduced pressure and the residue was crystallized from isopropanol to give 17.7 g (41%) of the hydrochloride salt of 3-pyridinevaleric acid, mp 144°–146° C.

EXAMPLE 56

Preparation of 3-pyridinevaleramide

3-Pyridinevaleramide was prepared from the reaction of the acid chloride of 3-pyridinevaleric acid with ammonium hydroxide as described below for 3-pyridinevaleramide. From 15.0 g of the acid chloride of 3-pyridinevaleric acid there was obtained 8.75 g (70%) of 3-pyridinevaleramide, mp 72°–75° C. The analytical sample was obtained from ethyl acetate-hexane, mp 77°–78° C.

EXAMPLE 57

Preparation of 3-pyridinepentanamine

3-Pyridinepentanamine was obtained from the borane reduction of 3-pyridinevaleramide as described below for 3-pyridinehexanamine. From 7.70 g of 5-3-pyridinevaleramide there was obtained 5.6 g (80%) of 3-pyridinepentanamine, bp 100°-108° C./0.2 mm.

EXAMPLE 58

Preparation of 3-pyridinehexanoic acid

To a suspension of 150 g of 4-(carboxy)butyl triphenylphosphonium bromide in 400 ml of dimethyl sulfate was added in portions, 33.6 g of a 50% dispersion of sodium hydride in mineral oil. The bath temperature was gradually raised to 75°-85° C. and held at this temperature for 30 minutes as the mixture became dark red. The internal temperature was lowered to 15°-19° C. as 32.1 g of nicotinaldehyde was added over 3 minutes. The reaction mixture was allowed to stir at room temperature for 3 hours, was diluted with 1.5 L of water, and was washed with 3×300 ml of ether. The aqueous layer was made strongly acidic with hydrochloric acid, was washed with dichloromethane and was made basic with sodium hydroxide solution, was neutralized with excess acetic acid to pH 5-6 and was extracted with 4×300 ml of dichloromethane. The combined extracts were dried over magnesium sulfate and evaporated finally under high vacuum at 60° C. bath temperature to remove dimethyl sulfoxide and acetic acid. The residue was recrystallized from acetonitrile-ether to give a total of 32.41 g (50%) of a mixture of double bond isomers in three crops melting between 65°-75° C.

A solution of 32.41 g of the above olefin mixture in 450 ml of isopropyl alcohol was hydrogenated successively over 3.5 g, 4.0 g, and 1.5 g of 10% palladium on carbon until total hydrogen uptake was 5 L. The reaction mixture was filtered and evaporated to give 31.25 g (95%) of 3-pyridinehexanoic acid, mp 100°-105° C. Recrystallization from ethyl acetate-hexane gave mp 103°-105° C. The hydrochloride salt was obtained from isopropanol-ether, mp 154°-156° C.

EXAMPLE 59

Preparation of 3-pyridinehexanamide

A solution of 14.19 g of 3-pyridinehexanoic acid in 42 ml of thionyl chloride was stirred at room temperature over night. The reaction mixture was evaporated with two successive 50 ml portions of toluene and the residue was added dropwise to 400 ml of concentrated ammonium hydroxide maintained between 0°-5° C. The resulting mixture was allowed to warm to room temperature over 4 hours, was diluted with water, and was extracted with 3×150 ml of dichloromethane. The combined organic layers were dried over potassium carbonate and concentrated to yield 11.75 g (83%) of 3-pyridinehexanamide, mp 64°-65° C.

EXAMPLE 60

Preparation of 3-pyridinehexanamine

To an ice-cold solution of 16.27 g of 3-pyridinehexanamide in 250 ml of dry tetrahydrofuran was added 300 ml of a 1M solution of borane in tetrahydrofuran. The mixture was heated to reflux over night, cooled, quenched with water, and made strongly acidic with 6N hydrochloric acid solution. The acidic solution was allowed to stand over night, made basic with sodium hydroxide solution, and was extracted with 3×150 ml of dichloromethane. The combined organic layers were dried over potassium carbonate, evaporated, and the residue was distilled to give 10.20 g (68%) of 3-pyridinehexanamine, bp 140°-150° C./0.2 mm.

EXAMPLE 61

Preparation of 4-pyridinebutanenitrile

4-Pyridinebutanenitrile was prepared according to the procedure employed in the synthesis of 3-pyridinebutanenitrile. From 73.1 g of the hydrobromide salt of 3-(4-pyridyl)propyl bromide there was obtained 19.35 g (51%) of 4-pyridinebutanenitrile, bp 140°-141° C./2.0 mm.

EXAMPLE 62

Preparation of 4-pyridinebutanamine

A solution of 30.0 g of 4-pyridinebutanenitrile in 200 ml of ethanol containing 7.5 ml of triethylamine was hydrogenated over 7.5 g of Raney cobalt at 100° C. and 1200 lbs. hydrogen pressure. The crude product obtained after filtration and concentration, was distilled to give 9.7 g (31%) of 4-pyridinebutanamine, bp 105°-112° C./0.8 mm. A second fraction (15.3 g, bp 112°-122° C.) consisted of a mixture by thin layer chromatography and was redistilled to give 4.74 g (15%) of 4-pyridinebutanamine, bp 95°-98° C./0.15 mm. The product was further characterized as the hydrochloride salt, mp 124°-125° C. (ethanolether).

EXAMPLE 63

Preparation of 4-pyridinevaleric acid

4-Pyridinevaleric acid was prepared according to the procedure employed in the preparation of 3-pyridinevaleric acid. From 56.0 g of the hydrobromide salt of 3-(4-pyridyl)propyl bromide there was obtained 10.4 g (24%) of 4-pyridinevaleric acid, mp 195°-200° C. The analytical sample was obtained from isopropanol, mp 200°-201° C.

EXAMPLE 64

Preparation of 4-pyridinevaleramide

4-Pyridinevaleramide was prepared using the procedures employed for 3-pyridinevaleramide. From 9.30 g of 4-pyridinevaleric acid there was obtained 5.3 g (69%), mp 123°-125° C. The analytical sample was obtained from tetrahydrofuran-hexane, mp 126°-127° C.

EXAMPLE 65

Preparation of 4-pyridinepentanamine

4-Pyridinepentanamine was prepared by the borane reduction of the amide 4-pyridinevaleramide as described for 3-pyridinehexanamine above. From 5.2 g 4-pyridinevaleramide there was obtained 3.5 g (74%) of 4-pyridinepentanamine, bp 140°-150° C./0.07 mm which was used without further purification in the preparation of N-[5-(4-pyridyl)pentyl]-2-(1-methylethyl)-11-oxo-11H-pyrido[2,1-b]quinazoline-8-carboxamide.

EXAMPLE 66

Preparation of 2-(4-pyridylthio)ethanamine dihydrobromide

A solution of 32.72 g of 4-mercaptopyridine and 61.0 g of 2-bromoethanamine hydrobromide in 200 ml of absolute ethanol was heated to reflux under an argon atmosphere for 2 hours. After cooling the precipitated product was collected and washed with ethanol to give 76.31 g of crude 2-(4-pyridylthio)ethanamine dihydrobromide, mp 250°–254° C. Recrystallization from ethanol (1500 ml) and water (150 ml) with a charcoal treatment afforded 63.09 g (68%) of 2-(4-pyridylthio)ethanamine dihydrobromide, mp 265°–268° C.

EXAMPLE 67

Preparation of 4-(4-pyridylthio)butanenitrile

A suspension of 16.0 g of 4-mercaptopyridine and 23.54 g of 4-bromobutyronitrile in 40 ml of absolute alcohol was heated to reflux under an argon atmosphere for 2 hours. The cool reaction mixture was diluted with 30 ml of ether and the solid was collected and recrystallized from ethanol-ether to give 24.9 g (67%) of the hydrobromide salt of 4-(4-pyridylthio)butanenitrile, mp 150°–154° C. Partitioning of the salt of 4-(4-pyridylthio)butanenitrile between dichloromethane and 3N sodium hydroxide solution and distillation of the residue obtained after concentration of the dichloromethane layer gave 16.16 g of the free base, bp 185° 1 C./0.1 mm.

EXAMPLE 68

Preparation of 4-(4-pyridylthio)butanamine

A solution of 14.35 g of 4-(4-pyridylthio)butanenitrile in 280 ml of 1 Molar borane in tetrahydrofuran was stirred over night at room temperature. The excess reagent was quenched by the careful addition of 100 ml of methanol. The reaction mixture was evaporated to dryness, diluted with 200 ml of methanol, evaporated, diluted with 100 ml of 6N hydrochloric acid and allowed to stand at room temperature for 72 hours. The resulting mixture was made strongly basic with 50% sodium hydroxide and was extracted with 4×150 ml of dichloromethane. The combined organic layers were dried over potassium carbonate, evaporated, and the residue was distilled to give 12.62 g (86%) of 4-(4-pyridylthio)butanamine, bp 180° C./0.1 mm.

EXAMPLE 69

Preparation of (1H-imidazol-1-yl)butanenitrile

A suspension of 17.0 g of imidazole, 25.0 g of 4-bromobutyrolnitrile, and 34.5 g of potassium carbonate in 60 ml of methyl ethyl ketone was heated at reflux for 18 hours. The reaction mixture was diluted with aqueous sodium hydroxide solution and was extracted with 3×100 ml of dichloromethane. The combined extract was dried over potassium carbonate, evaporated, and distilled. After collecting a fore-run of imidazole, 11.30 g (50%) of (1H-imidazol-1-yl)butanenitrile, bp 170° C./0.1 mm distilled.

EXAMPLE 70

Preparation of (1H-imidazol-1-yl)butanamine

A solution of 10.8 g of (1H-imidazol-1-yl)butanenitrile in 225 ml of methanol and 2.5 ml of triethylamine was hydrogenated over 2.5 g of Raney-Cobalt at 90° C. and a hydrogen pressure of 1000 psi. The crude product obtained after filtration and concentration was distilled to give 7.8 g (70%) of (1H-imidazol-1-yl)butanamine, bp 100°–103° C./0.1 mm. The dihydrochloride salt was crystallized from ethanol, mp 139°–141° C.

EXAMPLE 71

Preparation of 2-(1-methylethyl)-11-oxo-11H-pyrido[2,1-b]quinazoline-6-carboxylic acid A mixture of 13 g of 2-chloronicotinic acid, 9.9 g of 5-isopropylanthranilic acid and 0.1 g of potassium bromide in 10 ml of triglyme was heated gradually to a bath temperature of 140° C. After 2 hours a orange solid had separated, the reaction mixture was allowed to cool as 10 ml of ethanol were added, and the crude product was collected. This material was crystallized from acetic acid-water to give 9.3 g of a solid mp 173°–193° C., which was dissolved in 100 ml of acetic acid and heated to reflux for 1 hour. The solvent was evaporated and the residue was crystallized from isopropylalcohol to give 5.8 g (37%) of 2-(1-methylethyl)-11-oxo-11H-pyrido[2,1-b]quinazoline-6-carboxylic acid, mp 206°–210° C. The analytical sample gave mp 221°–223° C.

EXAMPLE 72

Preparation of 8-(1-methylethyl)-N-[4-(3-pyridyl)butyl]-11-oxo-11H-pyrido[2,1-b]quinazoline-2-carboxamide A solution of 1.50 g of 8-(1-methylethyl)-11-oxo-11H-pyrido[2,1-b]quinazoline-8-carboxylic acid, 0.80 g of 3-pyridinebutanamine and 1.5 g of diphenylphosphoryl azide in 22 ml of dry dimethylformamide was cooled in an ice bath as 0.73 ml of triethylamine was added to the reaction mixture all at once. The reaction mixture was allowed to come to room temperature over night, diluted with water and extracted with dichloromethane. The combined organic layers were washed with saturated sodium bicarbonate solution, dried over potassium carbonate and were evaporated. The residual oil was chromatographed on 120 g of silica gel eluting with 1% triethylamine, 2% ethanol, and 97% ethyl acetate. The product was acidified with ethanolic hydrochloric acid and recrystallized from isopropanol-ether to give 1.87 g (72%) of 8-(1-methylethyl)-N-[4-(3-pyridyl)butyl]-11-oxo-11H-pyrido[2,1-b]quinazoline-2-carboxamide, dihydrochloride, mp 247°–249° C.

EXAMPLE 73

Preparation of 2-(1-methylethyl)-11-oxo-11H-pyrido[2,1-b]quinazoline-8-carboxylic acid cyanomethyl ester A suspension of 20 g of 2-(1-methylethyl)-11-oxo-11H-pyrido[2,1-b]quinazoline-8-carboxylic acid, 6.3 ml of chloroacetonitrile and 13.2 g of potassium carbonate in 100 ml of dimethylformamide was stirred 18 hours at room temperature. The reaction mixture was diluted with 200 ml of water and the precipitated product collected to give 21.63 g (95%) of 2-(1-methylethyl)-11-oxo-11H-pyrido[2,1-b]quinazoline-8-carboxylic acid cyanomethyl ester, mp 186°–188° C.

EXAMPLE 74

Preparation of 2-(1-methylethyl)-N-[4-(3-pyridinyl)butyl]-11-oxo-11H-pyrido[2,1-b]quinazoline-6-carboxamide A solution of 2.82 g of 2-(1-methylethyl)-11-oxo-11H-pyrido[2,1-b]quinazoline-6-carboxylic acid, 2.75 g of diphenylphosphoryl azide, and 1.50 g of 3-pyridinebutanamine in 30 ml of dry dimethylformamide was cooled in an ice bath as 1.0 g of triethylamine was added to the mixture. The reaction mixture was allowed to warm to room temperature over 18 hours, was diluted with water and was extracted with dichloromethane. The combined organic layer was washed with dilute sodium carbonate solution, dried over potassium carbonate and evaporated to dryness. The residue was crystallized repeatedly from ethyl acetate to give 0.25 g (6%) of 2-(1-methylethyl)-N-[4-(3-pyridinyl)butyl]-11-oxo-11H-pyrido[2,1-b]quinazoline-6-carboxamide, mp 129°-130° C.

EXAMPLE 75

Preparation of 8-(1-methylethyl)-11-oxo-11H-pyrido[2,1-b]quinazoline-2-carboxylic acid 3-(3-pyridyl)propyl ester A suspension of 0.60 g of 8-(1-methylethyl)-11-oxo-11H-pyrido[2,1-b]quinazoline-2-carboxylic acid, 0.63 g of 3-(3-pyridyl)propyl bromide hydrobromide and 0.62 g of potassium carbonate in 50 ml of dimethylformamide was stirred at a bath temperature of 70° C. for three hours. The mixture was diluted with dichloromethane and washed successively with water, 10% sodium hydroxide, and water and was dried over K₂CO₃. The residue obtained after evaporation afforded 0.40 g of 8-(1-methylethyl)-11-oxo-11H-pyrido[2,1-b]quinazoline-2-carboxylic acid 3-(3-pyridyl)propyl ester, mp 111°-112° C.

EXAMPLE 76

Preparation of 2-[[(4-pyridyl)methyl]thio]ethanamine 34.1 g of sodium hydroxide was dissolved in 500 ml of ethanol under an argon atmosphere and 48.6 g of 2-mercaptoethanamine hydrochloride and 35 g of 4-chloromethylpyridine pyridine hydrochloride were added with ice bath cooling. The reaction mixture was allowed to warm to room temperature over 2 hours, was concentrated, diluted with 300 ml of water and was extracted with 3×150 ml of dichloromethane. The combined organic layers were washed with 100 ml of saturated brine, dried over potassium carbonate and were evaporated to a dark oil which was distilled. The fractions bp 120°-130° C./0.1 mm amounted to 30.68 g (85%) of 2-[[(4-pyridyl)methyl]thio]ethanamine.

EXAMPLE 77

Preparation of 2-[[(3-pyridyl)methyl]thio]ethanamine 16.8 g of sodium hydroxide was dissolved in 350 ml of ethanol and 17.2 g of 3-chloromethylpyridine hydrochloride and 23.7 g of 2-mercaptoethanamine hydrochloride were added with ice bath cooling. The reaction mixture was allowed to warm to room temperature over 2 hours, was concentrated, diluted with water, and extracted with 3×100 ml of dichloromethane. The combined organic layers were washed with saturated brine, dried over potassium carbonate and concentrated. The residue was distilled to give 12.30 g (70%) of 2-[[(3-pyridyl)methyl]thio]ethanamine, bp 115°-125° C./0.1 mm.

EXAMPLE 78

Preparation of (2-methyl-1H-imidazol-1-yl)butanenitrile 12.8 g of sodium hydroxide was dissolved in 12 ml of water and diluted with 150 ml of dimethylformamide containing 20.3 g of 2-methylimidazole. A solution of 50.0 g of 4-bromobutyronitrile in 100 ml of dimethylformamide was added slowly maintaining the temperature below 30° C. The resulting mixture was stirred overnight and was concentrated. The residue was taken up in 150 ml of brine and extracted with dichloromethane. The combined organic layers were dried over potassium carbonate and evaporated. The product was distilled. The early fractions were mostly 2-methylimidazole and were discarded. The main fraction 23.2 g, bp 160°-185° C./2.5 mm, was redistilled to give 14.7 g (31%) of (2-methyl-1H-imidazol-1-yl)-butanitrile, bp 140°-147° C./0.5 mm.

EXAMPLE 79

Preparation of (2-methyl-1H-imidazol-1-yl)butanamine

A solution of 14.7 g of (2-methyl-1H-imidazol-1-yl)butanenitrile in 3 ml of triethylamine and 200 ml of methanol was hydrogenated at 1000 lbs. hydrogen pressure and 90° C. over 3 g of Raney-Cobalt. The product obtained after evaporation of the solvents was distilled to give 10.6 g (70%) of (2-methyl-1H-imidazol-1-yl)butanamine, bp 105°-110° C./0.5 mm.

EXAMPLE 80

Preparation of α-methyl-3-pyridinepropanamine

A solution of 12.0 g of 4-(3-pyridinyl)-2-butanone hydrochloride, 3.38 g of sodium cyanoborohydride, and 42.78 g of ammonium acetate in 200 ml of methanol was stirred at room temperature for 2.5 days, acidified with dilute hydrochloric acid, and concentrated. The residue was dissolved in aqueous potassium carbonate solution and was extracted with dichloromethane. The residue obtained after evaporation of the dichloromethane was distilled to give 6.5 g (80%) of α-methyl-3-pyridinepropanamine, bp 126°-148° C./0.3 mm. The picrate was crystallized from methanol-ether; mp 146°-148° C.

EXAMPLE 81

Preparation of 4-(5-pyrimidinyl)-3-butyn-1-ol 4-(5-Pyrimidinyl)-3-butyn-1-ol was prepared according to the procedure described in Example 70 for 6-(5-pyrimidinyl)-5-hexyn-1-ol. From 20.0 g of 5-bromopyrimidine there was obtained 20.3 g of crude 4-(5-pyrimidinyl)-3-butyn-1-ol.

EXAMPLE 82

Preparation of (5-pyrimidine)butanol

A solution of 18.5 g of 4-(5-pyrimidinyl)-3-butyn-1-ol in 300 ml of isopropanol was hydrogenated over a total of 3.5 g of 10% palladium on carbon added in three portions. Evaporation of the solvent and distillation of the residue gave 15.2 g (80%) of 5-pyrimidinebutanol, bp 175°-180° C./0.5 mm.

EXAMPLE 83

Preparation 2-[4-(5-pyrimidinyl)butyl]-1H-isoindole-1,3-(2H)-dione

2-[4-(5-Pyrimidinyl)butyl]-1H-isoindole-1,3-(2H)-dione was prepared according to the procedure described for 2-[6-(5-pyrimidinyl)hexyl]-1H-isoindole-1,3-(2H)-dione in Example 72. From 14.8 g of 5-pyrimidinebutanol there was obtained 16.3 g (60%) of 2-[4-(5-pyrimidinyl)butyl]-1H-isoindole-1,3-(2H)-dione, mp 148°-149° C.

EXAMPLE 84

Preparation of 5-pyrimidinebutanamine

5-Pyrimidinebutanamine was prepared according to the procedure described in Example 73 for 5-pyrimidinehexanamine. From 15.8 g of 2-[4-(5-pyrimidinyl)butyl]-1H-isoindole-1,3(2H)-dione there was obtained 7.4 g (87%) of 5-pyrimidinebutanamine, bp 140°–150° C./0.3 mm. The picrate was crystallized from ethanol, mp 183°–184° C.

EXAMPLE 85

Preparation of 6-(5-pyrimidinyl)-5-hexyn-1-ol

A solution of 23.8 g of 5-bromopyrimidine and 17.7 g of 5-hexyn-1-ol in 59.5 ml of triethylamine and 240 ml of dichloromethane was degassed with argon and 200 mg of cuprous iodide followed by 2.1 g of bis(triphenylphosphine)palladium chloride were added. The resulting mixture was refluxed for 3 hours, diluted with dichloromethane, and washed with water. Evaporation of the solvent gave 31.7 g of crude product which was purified by chromatography over 400 g of silica gel, eluting with ethyl acetate to give 26.2 g of 6-(5-pyrimidinyl)-5-hexyn-1-ol.

EXAMPLE 86

Preparation of 5-pyrimidinehexanol

A solution of 25.3 g of 6-(5-pyrimidinyl)-5-hexyn-1-ol in 300 ml of isopropanol was hydrogenated over a total of 2.1 g of 10% palladium on carbon added in two portions. The residue was distilled to yield 22.8 g (88%) of 5-pyrimidinehexanol, bp 185°–196° C./0.35 mm.

EXAMPLE 87

Preparation of 2-[6-(5-pyrimidinyl)hexyl]-1H-isoindole-1,3-(2H)-dione

A. A solution of 20.6 g of 5-pyrimidinehexanol in 80 ml of dichloromethane was cooled in an ice bath as a solution of 12.3 ml of thionyl chloride in 40 ml of dichloromethane was added dropwise. The mixture was stirred at room temperature for 1 hour and at reflux temperature for 1 hour, was concentrated, azeotroped with toluene, diluted with dichloromethane and washed with water, saturated sodium bicarbonate, and brine. Evaporation gave 22.3 g of 6-(5-pyrimidinyl)hexylchloride.

B. A solution of 22.3 g of 6-(5-pyrimidinyl)hexyl chloride, 41.6 g of potassium phthalimide, and 1.8 g of potassium iodide in 180 ml of dimethylformamide was heated to a bath temperature of 130° C. for 1 hour. The mixture was diluted with water and was extracted with dichloromethane. The combined organic layers were washed with water and were dried over potassium carbonate. The residue obtained after evaporation was crystallized from ethyl acetate-hexane to give 24.7 g (71%) of 2-[6-(5-pyrimidinyl)hexyl]-1H-isoindole-1,3-(2H)-dione, mp 124°–126.5° C.

EXAMPLE 88

Preparation of (5-pyrimidine)hexanamine

A solution of 23.2 g of 2-[6-(5-pyrimidinyl)hexyl]-1H-isoindole-1,3-(2H)-dione and 14.6 ml of hydrazine hydrate in 320 ml of ethanol was heated to reflux for 3 hours. The cooled mixture was filtered and the filtrate was concentrated and dissolved in dichloromethne. The solution was washed with 5% sodium hydroxide, dried and evaporated to an oil which was evaportively distilled to yield 12.0 g (90%) of 5-pyrimidinehexanamine, bp 120°–128° C./0.6 mm.

EXAMPLE 89

Preparation of benzyl (1H-imidazol-1-yl)hexanoate

A. A mixture of 50.0 g of 6-bromohexanoic acid, 88 g of benzyl bromide, and 69 g of potassium carbonate in 500 ml of dimethylformamide was stirred overnight at room temperature. The reaction mixture was filtered, concentrated, and the residue was taken up in ether, washed with water and dried over sodium sulfate. The residue obtained after evaporation was distilled to give 63 g (85%) of benzyl 6-bromohexanoate.

B. To a suspension of 9.74 g of 57% sodium hydride in 100 ml of dimethylformamide was added a solution of 15.0 g of imidazole in 500 ml of dimethylformamide at a temperature of 15°–25° C. The resulting mixture was heated to 60° C. for 1 hour, was cooled to room temperature and 62.8 g of benzyl 6-bromohexanoate was added. The mixture was heated to 60° C. for two hours, allowed to stand overnight at room temperature, and was evaporated. The residue was taken up in aqueous hydrochloric acid, washed with ether, made basic with sodium hydroxide and extracted with dichloromethane. The combined organic layers were dried, evaporated and distilled to yield 45.1 g (75%) of benzyl (1H-imidazol-yl)hexanoate.

EXAMPLE 90

Preparation of (1H-imidazol-1-yl)hexanoic acid

A solution of 45.1 g of benzyl (1H-imidazol-1-yl)hexanoate in 200 ml of isopropanol was hydrogenated over 10% palladium on carbon. Filtration and evaporation of the solvent gave 24.9 g (80%) of (1H-imidazol-1-yl)hexanoic acid, mp 135°–137° C.

EXAMPLE 91

Preparation of (1H-imidazol-1-yl)hexanamine

A. A solution of 10.4 g of (1H-imidazol-1-yl)hexanoic acid hydrochloride in 50 ml of thionylchloride was stirred two hours at room temperature and was evaporated. The residue was taken up in toluene and evaporated two times and was added to an ice cold ammonium hydroxide solution. After 18 hours, the solvent was evaporated, the residue dissolved in water and extracted with dichloromethne. The extracts afforded 6.0 g of a solid which was crystallized from dichloromethane-hexane to give 3.9 g (45%) of (1H-imidazol-1-yl)hexanamide, mp 90°–91° C.

B. A solution of 3.9 g of (1H-imidazol-1-yl)hexanamide in 75 ml of tetrahydrofuran was cooled in an ice bath as 75 ml of 1 molar borane in tetrahydrofuran was added. The resulting mixture was heated to reflux overnight, was diluted with water and dilute hydrochloric acid and allowed to stand overnight. The mixture was made basic with 50% sodium hydroxide and was extracted with dichloromethne. The residue obtained by evaporation of the organic layers was distilled to yield 3.1 g (86%) of (1H-imidazol-1-yl)hexanamine, bp 145°–155° C./0.1 mm.

EXAMPLE 92

Preparation of 3-pyridine heptanamine

A. A solution of 26.6 g of 3-pyridinehexanoic acid in 200 ml of dry tetrahydrofuran was cooled in an ice bath as 488 ml of 1 molar borane in tetrahydrofuran was added slowly. The reaction mixture was gradually brought to reflux temperature and was heated overnight. The excess reagent was quenched by the careful addition of 100 ml of methanol and the mixture was concentrated. The residue was diluted with excess 6N hydrochloric acid, allowed to stand overnight, made basic with 50% sodium hydroxide, and extracted with dichloromethane. The combined organic layers were dried over potassium carbonate, and evaporated to an oil which was distilled to give 22.6 g (92%) of 6-(3-pyridyl)hexanol, bp 180°-200° C./0.2 mm.

B. A solution of 22 g of 6-(3-pyridyl)hexanol in 100 ml of chloroform was cooled in an ice bath and treated with a solution of 21.9 g of thionyl chloride in 50 ml of chloroform. The reaction mixture was allowed to warm to room temperature over 1 hour, was heated to a bath temperature of 60° C. for 1 hour and was concentrated. The residue was taken up in chloroform, washed with saturated potassium carbonate, dried, and evaporated. The residue was distilled to give 20.5 g (84%) of 6-(3-pyridyl)hexylchloride, bp 180°-190° C./0.15 mm.

C. A mixture of 4.0 g of potassium cyanide, 0.85 g of potassium iodide and 10.1 g of 6-(3-pyridyl)hexyl chloride in 100 ml of dimethylformamide was heated at 100° C. overnight. The reaction mixture was diluted with 200 ml of water and was extracted with dichloromethane. The combined organic layers were washed with water, dried over potassium carbonate and were evaporated. The residue was distilled to give 8.1 g (84%) of 3-pyridine heptanenitrile.

D. A solution of 7.1 g of 3-pyridine heptanenitrile in 100 ml of tetrahydrofuran was cooled in an ice bath and treated with 113 ml of 1 molar borane in tetrahydrofuran. After 30 minutes, the reaction mixture was heated to reflux. After 18 hours, the mixture was cooled, treated with 100 ml of methanol, evaporated and treated with 6N hydrochloric acid. After standing overnight at room temperature, the mixture was heated to 95° C. for 15 minutes, diluted with water and potassium carbonate, and extracted with dichloromethane. The organic layers were dried over potassium carbonate, and evaporated to give 5.6 g of an oil. The oil was treated with acetic anhydride overnight, was diluted with water and extracted with dichloromethane. The combined organic layers were dried over potassium carbonate and evaporated. The residue was distilled to give 5.8 g of N-[7-(3-pyridyl)heptyl]acetamide bp 145°-155° C./0.1 mm.

E. A solution of 5.1 g of N-[7-(3-pyridyl)heptyl]acetamide was heated to reflux in diluted hydrochloric acid overnight. The mixture was cooled, made basic with 50% sodium hydroxide solution and was extracted with dichloromethane. The combined organic layers were dried over potassium carbonate and were evaporated. The residue was distilled to give 3.4 g of 3-pyridine heptanamine, bp 175°-180° C./0.4 mm.

EXAMPLE 93

Preparation of [(2,3-dimethyl-11-oxo-11H]-pyrido[2,1-b]quinazoline-8-carboxylic acid cyanomethyl ester A mixture of 15.0 g of 2,3-dimethyl-11-oxo-11H-pyrido[2,1-b]quinazoline-8-carboxylic acid, 10.2 g of potassium carbonate, 4.9 ml (5.8 g) of chloroacetonitrile and 150 ml of N,N-dimethylformamide was heated at 65° for 18 hours. The cooled reaction mixture was poured into 800 ml of water and the resulting solid was collected by filtration. This was washed with water and dried to give 14.4 g (84%) of crude product as yellow crystals, m.p. 175°-179° dec. Recrystallization from acetonitrile gave 8.7 g (51%) of the analytical sample of [(2,3-dimethyl-11-oxo-11H]-pyrido[2,1-b]quinazoline-8-carboxylic acid cyanomethyl ester, m.p. 182°-184° dec.

EXAMPLE 94

Preparation of 2-hydroxy-11-oxo-11H-pyrido[2,1-b]quinazoline-8-carboxylic acid cyanomethyl ester A suspension of 5.00 g of 2-hydroxy-11-oxo-11H-pyrido[2,1-b]quinazoline-8-carboxylic acid, 1.7 ml of chloroacetonitrile and 2.3 g of sodium bicarbonate in 70 ml of dimethylformamide was stirred at room temperature for 12 days. The reaction mixture was diluted with water and the precipitated product collected to give 5.4 g, mp 260°-262° C.,. Recrystallization from dimethylformamide-water afforded 4.0 g (68%), of 2-hydroxy-11-oxo-11H-pyrido[2,1-b]quinazoline-8-carboxylic acid cyanomethyl ester, mp 265°-267° C.

EXAMPLE 95

Preparation of 1-(3-aminopropyl)pyridinium bromide hydrobromide

A solution of 16.5 g of 3-bromopropanamine hydrobromide and 6.0 ml (5.9 g) of pyridine in 75 ml of ethanol was heated under reflux for 18 hours. The cooled reaction was filtered and the solid was washed with ethanol to give 17.0 g (76%) of 1-(3-aminopropyl)-pyridinium bromide hydrobromide as colorless crystals, mp 178°-179°. The analytical sample was obtained by recrystallization from methanol and had mp. 176°-179° C.

EXAMPLE 96

Preparation of 1-(4-aminobutyl)pyridinium bromide hydrobromide

A solution of 17.4 g of 4-bromobutanamine hydrobromide and 6.0 ml (5.9 g) of pyridine in 75 ml of ethanol was heated under reflux for 18 hours. The reaction was cooled and the resulting solid was collected and recrystallized from ethanol to give 3.4 g (15%) of the analytical sample as colorless crystals, 1-(4-aminobutyl)-pyridinium bromide hydrobromide mp 219° (decomposition).

EXAMPLE 97

Preparation of 1-[2-(2-methyl-1,3-dioxolan-2-yl)propyl]-1H-imidazole

A suspension of 29.0 g of imidazole and 23.1 g of sodium methoxide in 385 ml of dimethylformamide was stirred for 30 minutes and cooled in an ice bath as 85.8 g of 3-(2-methyl-1,3-dioxolan-2-yl)propyl bromide was added dropwise. The resulting mixture was maintained at room temperature for 30 minutes and heated to reflux for 1 hour. The solvent was evaporated in vacuo, the residue diluted with acetone and filtered. The filtrate was concentrated and the residue was distilled to afford 37.9 g (47%) of 1-[2-(2-methyl-1,3-dioxolan-2-yl)propyl]-1H-imidazole as a colorless oil, bp 102°-108° C./0.1 mm.

EXAMPLE 98

Preparation of 5-(1H-imidazol-1-yl)-2-pentanone

A solution of 48.4 g of 1-[3-(2-methyl-1,3-dioxolan-2-yl)-propyl]-1H-imidazole in 615 ml of 1M hydrochloric acid was stirred overnight. The reaction mixture was concentrated to half volume under reduced pressure and the solution was made basic with sodium hydroxide and extracted with dichloromethane. The combined organic layers were dried over potassium carbonate and the residue obtained after concentration was distilled to yield 30.17 g (77%), bp 110°–121° C./0.1 min. A sample was further purified on silica gel thick layer plates eluting with 9% methanol-dichloromethane to give an analytical sample of 5-(1H-imidazol-1-yl)-2-pentanone.

EXAMPLE 99

Preparation of alpha-methyl-1H-imidazole-1-butanamine

A solution of 8.3 g of 5-(1H-imidazol-1-yl)-2-pentanone, 44.0 g of ammonium acetate, and 3.5 g of sodium cyanoborohydride in 200 ml of methanol was stirred at room temperature for 2.5 days. The reaction mixture was acidified with hydrochloric acid and concentrated to dryness. The residue was taken up in potassium carbonate solution and extracted with dichloromethane. The combined extracts were dried over potassium carbonate and evaporated and the residue was distilled to give 4.6 g (55%) of alphamethyl-1H-imidazole-1-butanamine, bp 110°–117° C./0.25 mm.

EXAMPLE 100

Preparation of N-alpha-dimethyl-1H-imidazole-1-butanamine

A solution of 10.0 g of 5-(1H-imidazol-1-yl)-2-pentanone, 13.0 g of methylamine hydrochloride and 4.2 g of sodium cyanoborohydride in 200 ml of methanol was stirred for 3 days. The reaction was quenched with dilute hydrochloric acid and evaporated. The residue was diluted with aqueous potassium carbonate and extracted with dichloromethane. The combined organic layers were dried over potassium carbonate and evaporated to give 10.2 g of an oil which was distilled to give 9.0 g (90%) of N-alphadimethyl-1H-imidazole-1-butanamine, bp 110°–120° C./0.1 mm. Picrate, mp 112°–114° C.

EXAMPLE 101

Preparation of N-[4-(1H-imidazol-1-yl)butyl]formamide

A solution of 53.2 g of (1H-imidazol-1-yl)butanamine in 820 ml of formic acid was cooled in an ice bath and 266 ml of acetic anhydride were added dropwise. The reaction mixture was stirred for 3 days and concentrated in vacuo. The residue was partitioned between aqueous potassium carbonate and dichloromethane and the organic layer was dried over potassium carbonate. The residue obtained after evaporation was distilled to give 58.8 g (87%) of N-[4-(1H-imidazol-1-yl)butyl]formamide, bp 165°–180° C./0.3 mm which was used directly in the next step.

EXAMPLE 102

Preparation of 4-(1H-imidazol-1-yl)-N-methylbutanamine

A solution of 58.8 g of N-[4-(1H-imidazol-1-yl)butyl]formamide in 480 ml of dry tetrahydrofuran was treated with 87.0 ml of 10 Molar borane methyl sulfide complex in tetrahydrofuran. The reaction mixture was heated to reflux for 18 hours under an argon atmosphere, cooled in an ice bath and quenched with 400 ml of methanol. The solvent was removed, the methanol addition and evaporation repeated, and the residue was made acidic with hydrochloric acid and was stirred over night. The mixture was made basic with sodium hydroxide solution and was extracted with dichloromethane. The combined organic layers were dried over potassium carbonate and evaporated to give an oil which was distilled to give 35.9 g (68%) of 4-(1H-imidazol-1-yl)-N-methylbutanamine, bp 130°–135° C./0.3 mm. The product was further characterized as the picrate, mp 111–113.

EXAMPLE 103

Preparation of 4-(5-pyrimidinyl)-2-butanone hydrochloride

A solution of 31.80 g of 5-bromopyrimidine, 20.0 g of sodium bicarbonate, and 21.65 g of 3-butene-1-ol in 150 ml of dimethylformamide was degassed with a stream of argon for 30 minutes and 0.75 g of palladium acetate was added. The reaction flask was evacuated and filled with argon three times and the bath temperature was raised to 120° C. for 4 hours. The reaction mixture was diluted with 400 ml of ethyl acetate and was filtered. The filtrate was concentrated and finally evaporatively distilled to give 27.36 g of an oil, bp 100°–110° C., 3 mm. The crude product was acidified with hydrochloric acid and crystallized from ethanol-ether to give 19.22 g (51%) of 4-(5-pyrimidinyl)-2-butanone hydrochloride, mp 103°–106° C.

EXAMPLE 104

Preparation of rac.-alpha-methyl-5-pyrimidinepropanamine

A solution of 10.0 g of 4-(5-pyrimidinyl)-2-butanone hydrochloride, 42.5 g of ammonium acetate and 3.37 g of sodium cyanoborohydride in 200 ml of methanol was stirred at room temperature for 2.5 days. The reaction mixture was acidified and concentrated and the residue was dissolved in water, made basic with dilute sodium hydroxide solution and extracted with dichloromethane. The combined organic layers were dried over potassium carbonate and evaporated to give 7.5 g of an oil. Formation of the hydrochloride salt and crystallization from ethanol-ether gave 2.47 g of rac.-alpha-methyl-5-pyrimidinepropanamine, mp 163°–165° C.

EXAMPLE 105

Preparation of 6-(3-pyridinyl)-5-hexyn-1-ol

A dry 250 ml B 3-neck flask was fitted with a gas inlet tube extending nearly to the bottom of the flask and was charged with 9.81 ml of 3-bromopyridine, 11.8 g of 5-hexyn-1-ol, 40 ml of distilled triethylamine and 60 ml of dichloromethane. The mixture was degassed with argon for 15 minutes and 0.70 g of bis(triphenylphosphine)palladium dichloride and 0.13 g of cuprous iodide were added. The flask was evacuated and filled three times with argon and the reaction was heated to reflux for 2 hours. The cooled mixture was diluted with dichloromethane and was washed with water and brine, dried (potassium carbonate) and concentrated to 20 g of a dark red oil which was used directly in the next step. A portion was chromatographed over 70 g of silica gel eluting with 1:1 ethyl acetate-hexane containing 1% triethylamine to yield a colorless oil which was evaporatively distilled, bp 145°–150° C./0.1 mm to give an analytical sample of 6-(3-pyridinyl)-5-hexyn-1-ol.

EXAMPLE 106

Preparation of 6-(3-thiophene)-5-hexyn-1-ol 6-(3-Thiophene)-5-hexyn-1-ol was prepared in the same manner, as described in Example 105, starting with 16.0 g of 3-bromothiophene, 11.8 g of 5-hexyn-1-ol, 3.0 g of bistriphenylphosphine)palladium dichloride and 0.290 g of cuprous chloride in 165 ml of dichloromethane and 41 ml of triethylamine. The crude product was purified by high pressure liquid chromatography eluting with 0.75% methanol-dichloromethane to give 8.9 g (48%) of a colorless oil which was used directly. A portion was rechromatographed on silica gel thick layer plates to give the analytical sample of 6-(3-thiophene)-5-hexyn-1-ol.

EXAMPLE 107

Preparation of 3-thiophenehexanol

3-Thiophenehexanol was prepared by reduction of 8.4 g of 6-(3-thiophenyl)-5-hexyn-1-ol, in 100 ml of ethanol over 1.0 g of 10% palladium/carbon at atmospheric pressure. After 8 hours a second catalyst loading was added and the reduction continued over night. The residue obtained after filtration and evaporation of the solvent was evaporatively distilled to give 6.9 g (80%) of 3-thiophenehexanol, bp 135°–147° C./0.2 mm.

EXAMPLE 108

Preparation of 3-pyridinehexanol

3-Pyridinehexanol was prepared by hydrogenation of 20.0 g of the crude 6-(3-pyridinyl)-5-hexyn-1-ol, prepared above in Example 105, dissolved in 200 ml of isopropyl alcohol over 2.0 g of 10% palladium on carbon at 1 atmosphere. The crude product obtained after filtration of the catalyst and evaporation of the solvent was evaporatively distilled to yield 15.8 g (89%) of 3-pyridinehexanol as a yellow oil, bp 120°–150° C./0.2 mm which was 90% pure by gas chromatography analysis.

EXAMPLE 109

Preparation of 2-[6-(3-pyridinyl)hexyl]-1H-isoindole-1,3(2H)-dione

A suspension of 9.8 g of 3-pyridinehexyl chloride and 18.4 g of potassium phthalimide in 130 ml of dimethylformamide was heated to a bath temperature of 130° C. in the presence of 0.83 g of potassium iodide. After 1 hour, the reaction was allowed to cool, was diluted with water and extracted with ether. The combined organic layers were dried over sodium sulfate and concentrated to give a pink solid. Recrystallization from ethanol gave 9.5 g (62%) of 2-[6-(3-pyridinyl)hexyl]-1H-isoindole-1,3(2H)-dione as pink solid, mp 90°–92° C. The mother liquors afforded an additional 3.15 g (21%) of 2-[6-(3-pyridinyl)hexyl]-1H-isoindole-1,3(2H)-dione, mp 89°–92° C.

EXAMPLE 110

Preparation of 6-pyridinehexanamine

A solution of 81.9 g of 2-[6-(3-pyridinyl)hexyl]-1H-isoindole-1,3(2H)-dione in 1.1 L of ethanol and 51.7 ml of hydrazine hydrate was refluxed for 3 hours. The mixture was filtered and washed well with ethanol. The filtrate was concentrated. The residue was dissolved in dichloromethane and washed with 2.5N sodium hydroxide and dried over potassium carbonate. The residue obtained after concentration was distilled to give 42.4 g (90%) of 6-pyridinehexanamine, bp 125°–130° C./0.3 mm which was 98.5% pure by gas chromatography analysis.

EXAMPLE 111

Preparation of 6-(3-quinolinyl)-5-hexyn-1-ol 6-(3-Quinolinyl)-5-hexyn-1-ol was prepared in the manner described above in Example 105 starting with 15.0 g of 3-bromoquinoline, 8.5 g of 5-hexyn-1-ol, 1.05 g of bis(triphenylphosphine)palladium dichloride and 0.10 g of cuprous iodide in 115 ml of dichloromethane and 28.5 ml of triethylamine. The crude product was chromatographed on a preparative high pressure liquid chromatograph eluting with 2.5% methanol-dichloromethane to give 14.4 g (89%) of 6-(3-quinolinyl)-5-hexyn-1-ol as a colorless oil. A portion was purified further on a silica thick layer plate eluting with 10% methanol-dichloromethane and solidified on drying, mp 47°–48° C.

EXAMPLE 112

Preparation of 3-quinolinehexanol

3-Quinolinehexanol was prepared by reduction of 13.5 g of 6-(3-quinolinyl)-5-hexyn-1-ol over 1.0 g of 10% palladium on carbon at 1 atmosphere of hydrogen. The crude product obtained after filtration and evaporation was chromatographed over silica gel by high pressure liquid chromatography eluting with 2% methanol-dichloromethane. The first product to elute amounted to 0.95 g which was evaporatively distilled to yield 0.76 g (6%) of 6-[3-(1,2,3,4-tetrahydro)-quinolinyl]hexanol, bp 180°–185° C./0.1 mm. The second product to elute amounted to 9.1 g which was evaporatively distilled to give 8.3 g (61%) of 3-quinolinehexanol, bp 195°–205° C. 0.25 mm.

EXAMPLE 113

Preparation of 2-[6-(3-quinolinyl)hexyl]-1H-isoindole-1,3-(2H)-dione

A solution of 7.8 g of 3-quinolinehexanol in 35 ml of dry dichloromethane was treated dropwise with a solution of 6.07 g of thionyl chloride in 15 ml of dichloromethane. The reaction mixture was heated to reflux for 1 hour and evaporated to dryness. The residue was dissolved in dichloromethane, washed successively with water, saturated sodium bicarbonate solution and brine, dried over potassium carbonate and evaporated to give 8.3 g of crude 6-(3-quinolinyl)hexylchloride. A suspension of 8.3 g of 6-(3-quinolinyl)hexylchloride, 12.6 g of potassium phthalimide, and 0.50 g of potassium iodide in 60 ml of dimethylformamide was heated to a bath temperature of 130° C. for one hour. The cooled mixture was diluted with water and extracted with dichloromethane. The combined organic layers were washed with water, dried over potassium carbonate and evaporated. The crude solid was crystallized from ethyl acetate-hexane to give 9.9 g (82%) of 2-[6-(3-quinolinyl)hexyl]-1H-isoindole-1,3-(2H)-dione, mp 90°–91° C. An analytical sample was obtained from toluene, mp 95.5°–96.5° C.

EXAMPLE 114

Preparation of 3-quinolinehexanamine

3-Quinolinehexanamine was prepared in the same manner as described in Example 110, starting from 4.4 g of 2-[6-(3-quinolinyl)hexyl]-1H-isoindole-1,3(2H)-dione and 2.5 g of hydrazine hydrate in 60 ml of ethanol. The crude product was evaporatively distilled to give 2.5 g (89%) of 3-quinolinehexanamine, bp 144°–155° C./0.1 mm. Bis picrate mp 225°–226° C.

EXAMPLE 115

Preparation of 6-(3-pyridinyl)-5-hexynenitrile

Argon was passed through a solution of 45 ml of 3-bromopyridine and 49.61 g of 5-hexynenitrile in 500 ml of dichloromethane and 150 ml of dry triethylamine for 15 minutes and 3.0 g of bis(triphenylphosphine)palladium dichloride and 0.45 g of cuprous iodide were added. The reaction flask was evacuated and refilled with argon and was heated to reflux for 12 hours. The resulting mixture was diluted with 1 L of dichloromethane and washed with 2×300 ml of water, 1×300 ml brine, dried over potassium carbonate and concentrated. The residue was distilled to afford 62.82 g (79%) of 6-(3-pyridinyl)-5-hexynenitrile as a yellow oil, bp 140°–170° C./0.2 mm., suitable for use in the next step. A portion was purified by chromatography over silica gel eluting with 1:1 ethyl acetate-hexane containing 1% triethylamine and was redistilled to give an analytical sample of 6-(3-pyridinyl)-5-hexynenitrile.

EXAMPLE 116

Preparation of 6-(3-pyridinyl)hexanenitrile

A solution of 62.82 g of 6-(3-pyridinyl)-5-hexynenitrile in 500 ml of 2-propanol was hydrogenated over 3.0 g of 10% palladium on carbon at atmospheric pressure. Two additional 3.0 g charges of catalyst were added as the rate of hydrogen uptake slowed. After two days, the reaction mixture was filtered concentrated, the residue was evaporatively distilled and the distillate was dissolved in 300 ml of 2-propanol and was reduced over 3.0 g of 10% palladium on carbon. Filtration, evaporation, and distillation gave 52.15 g (82%) of 6-(3-pyridinyl)hexanenitrile, bp 150°/0.3 mm which gave a main peak consisting of 93% of the total by gas chromatography analysis. A portion was further purified by silica gel chromatography eluting with 1:1 ethyl acetate-hexane containing 1% triethyl amine and was evaporatively distilled to give an analytical sample.

EXAMPLE 117

Preparation of 3-Pyridinehexanamine

A solution of 52.15 g of 3-pyridinehexanenitrile in 600 ml of methanol and 13 ml of triethylamine was hydrogenated over 13 g of Raney cobalt at an initial hydrogen pressure of 1000 psi and 100° C. The cooled mixture was filtered and concentrated. The residue was distilled to give 46.5 g (87%) of 3-pyridinehexanamine, bp 102°–107° C./0.2 mm. This material was purified through its phthalimide which was formed by reaction with 39.53 g of phthalic anhydride in 300 ml of glacial acetic acid at reflux overnight. The residue obtained after evaporation of the solvent was dissolved in 300 ml of ethyl acetate, washed with dilute sodium hydroxide and sodium bicarbonate, dried over potassium carbonate and concentrated. The residue was crystallized from ethyl acetate-hexane to give 62.87 g (77%) of 2-[6-(3-pyridinyl)hexyl]-1H-isoindole-1,3(2H)-dione, mp 89°–92° C. A solution of this material in 880 ml of ethanol and 33 ml of hydrazine hydrate was heated to reflux for 3 hours. The cooled mixture was filtered and concentrated. The residue was taken up in 500 ml of dichloromethane and was washed with 10% sodium hydroxide and dried over potassium carbonate. The residue obtained after concentration was distilled to give 31.6 g (60% based on starting nitrile) of 3-pyridinehexanamine, bp 140°–150° C./0.3 mm which gave a single peak on gas chromatography.

EXAMPLE 118

| | TABLET FORMULATION (Wet granulation) | | | |
|---|---|---|---|---|
| Item | Ingredient | mg/tablet | mg/tablet | mg/tablet |
| 1. | N—[4-(1H—imidazol-1-yl)butyl]-2-(1-methylethyl-11-oxo-11H—pyrido[2,1-b]quinazoline-8-carboxamide | 100 | 250 | 500 |
| 2. | Lactose | 98.5 | 147.5 | 170 |
| 3. | Polyvinyl pyrrolidone | 15 | 30 | 40 |
| 4. | Modified starch | 15 | 30 | 40 |
| 5. | Corn starch | 15 | 30 | 40 |
| 6. | Magnesium stearate | 1.5 | 2.5 | 5 |
| | Weight of tablet | 245 mg | 490 mg | 795 mg |

Procedure:
(1) Mix items 1, 2, 4 and 5 in a suitable mixer, granulate with polyvinyl pyrrolidone and dissolve in water/alcohol. Dry the granulation. Mill the dry granulation through a suitable mill.
(2) Add magnesium stearate and compress on a suitable press.

EXAMPLE 119

| | TABLET FORMULATION (Wet granulation) | | | |
|---|---|---|---|---|
| Item | Ingredient | mg/tablet | mg/tablet | mg/tablet |
| 1. | N—[4-(1H—imidazol-1-yl)butyl]-2-(1-methylethyl)-11-oxo-11H—pyrido[2,1-b]quinazoline-8-carboxamide | 100 | 250 | 500 |
| 2. | Lactose | 147.5 | 100 | 97.5 |

-continued

TABLET FORMULATION
(Wet granulation)

| Item | Ingredient | mg/tablet | mg/tablet | mg/tablet |
|---|---|---|---|---|
| 3. | Pregelatinized starch | 25 | 30 | 60 |
| 4. | Modified starch | 25 | 50 | 60 |
| 5. | Corn starch | 25 | 50 | 60 |
| 6. | Magnesium stearate | 2.5 | 5 | 7.5 |
|  | Weight of tablet | 325 mg | 500 mg | 785 mg |

Procedure:
(1) Mix items 1, 2, 3, 4 and 5 in a suitable mixer, granulate with water, and dry over night in a suitable oven. Mill through suitable mill.
(2) Mix with item 6 and compress on a suitable press.

EXAMPLE 120

| | CAPSULE FORMULATION | | | |
|---|---|---|---|---|
| Item | Ingredient | mg/capsule | mg/capsule | mg/capsule |
| 1. | N—[4-(1H—imidazol-1-yl)butyl]-2-(1-methylethyl)-11-oxo-11H—pyrido[2,1-b]quinazoline-8-carboxamide | 100 | 250 | 500 |
| 2. | Lactose | 99 | 148 | — |
| 3. | Corn starch | 20 | 30 | 57 |
| 4. | Talc | 5 | 10 | 15 |
| 5. | Magnesium stearate | 1 | 2 | 3 |
|  | Fill weight of capsule | 225 mg | 440 mg | 575 mg |

Procedure:
(1) Mix items 1, 2, and 3 in a suitable mixer. Mill through a suitable mill.
(2) Mix the mixture in Step 1 with item 4 and 5 and fill on a suitable machine.

I claim:
1. A compound of the formula

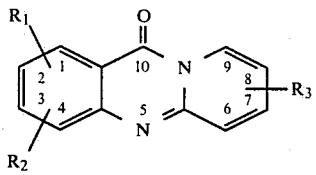

wherein $R_1$ and $R_2$, independently, are hydrogen, lower alkyl, lower alkoxy, hydroxy or halogen, and $R_3$ is in the 6-, 7- or 8-ring position and is

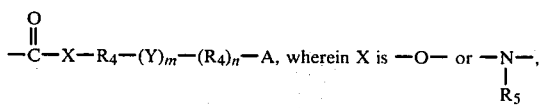

wherein $R_5$ is hydrogen or lower alkyl, $R_4$ is lower alkylene, Y is —O— or —S—, m is zero or 1, n is zero or 1, and A is an unsubstituted or substituted aromatic 5- or 6-membered heterocyclic group selected from the group consisting of pyridyl, pyrimidinyl, imidazolyl, furyl, thienyl thiazolyl, oxazolyl, isoxazolyl, pyrazinyl, quinolinyl, isoquinolinyl, quinazolinyl, 1,2,4-triazinyl, 1,2,4-triazolyl, benzimidazolyl and pyridazinyl and wherein the substituents are selected from the group consisting of straight- and branched-chain lower alkyl, straight- and branched-chain lower alkoxy, halogen and nitro, provided that when A is linked through a heterocyclic nitrogen, m and n must each be zero, or a pharmaceutically acceptable acid addition salt thereof.

2. A compound in accordance with claim 1, wherein X is $$-\text{N}-,$$
$$\quad \text{R}_5$$

3. A compound in accordance with claim 2, wherein A is 3-pyridyl, 4-pyridyl or imidazol-1-yl.

4. A compound in accordance with claim 3, wherein $R_1$ is in the 2-position, $R_2$ is in the 3-position, and $R_3$ is in the 8-position.

5. A compound in accordance with claim 4, wherein $R_1$ is lower alkyl, $R_2$ is hydrogen, $R_4$ is lower alkylene of 4–6 carbon atoms, and m and n are zero.

6. A compound in accordance with claim 5, wherein $R_1$ is isopropyl.

7. A compound in accordance with claim 4, wherein $R_1$ is hydroxy.

8. A compound in accordance with claim 1, N-[4-(1H-imidazol-1-yl)butyl]-2-(1-methylethyl)-11-oxo-11H-pyrido[2,1-b]quinazoline-8-carboxamide.

9. A compound in accordance with claim 1, 2-(1-methylethyl)-N-[6-(3-pyridyl)hexyl]-11-oxo-11H-pyrido[2,1-b]quinazoline-8-carboxamide.

10. A compound in accordance with claim 1, 2-(1-methylethyl)-N-[4-(3-pyridyl)butyl]-11-oxo-11H-pyrido[2,1-b]quinazoline-8-carboxamide.

11. A compound in accordance with claim 1, N-[5-(1H-imidazol-1-yl)pentyl]-2-(1-methylethyl)-11-oxo-11H-pyrido[2,1-b]quinazoline-8-carboxamide.

12. A compound in accordance with claim 1, N-[4-(4-pyridyl)butyl-2-(1-methylethyl)-11-oxo-11H-pyrido[2,1-b]quinazoline-8-carboxamide.

13. A compound in accordance with claim 1,2-(1-methylethyl)-N-[4-(3-pyridyloxy)butyl]11-oxo-11H-pyrido[2,1-b]quinazoline-8-carboxamide.

14. A compound in accordance with claim 1, N-[2-(4-pyridylthio)ethyl]-2-(1-methylethyl)-11-oxo-11H-pyrido[2,1-b]quinazoline-8-carboxamide.

15. A compound in accordance with claim 1, N-[5-(3-pyridyl)pentyl]-2-(1-methylethyl)-11-oxo-11H-pyrido[2,1-b]quinazoline-8-carboxamide.

16. A compound in accordance with claim 1, N-[5-(4-pyridyl)pentyl]-2-(1-methylethyl)-11-oxo-11H-pyrido[2,1-b]quinazoline-8-carboxamide.

17. A compound in accordance with claim 1, 2-methoxy-N-[4-(3-pyridyl)butyl]-11-oxo-11H-pyrido[2,1-b]quinazoline-8-carboxamide.

18. A compound in accordance with claim 1, 2-(1-methylethyl)-N-[4-(5-pyrimidyl)butyl]-11-oxo-11H-pyrido[2,1-b]quinazoline-8-carboxamide.

19. A compound in accordance with claim 1, N-[4-(2-methyl-1H-imidazol-1-yl)butyl]-2-(1-methylethyl)-11-oxo-11H-pyrido[2,1-b]quinazoline-8-carboxamide.

20. A compound in accordance with claim 1, N-[4-(3-pyridyl)butyl]-11-oxo-11H-pyrido[2,1-b]quinazoline-8-carboxamide.

21. A compound in accordance with claim 1, 2-hydroxy-N-[4-(3-pyridyl)butyl]-11-oxo-11H-pyrido[2,1-b]quinazoline-8-carboxamide.

22. A compound in accordance with claim 1, 2-(1-methylethyl)-N-[3-(3-pyridyl)propyl]-11-oxo-11H-pyrido[2,1-b]quinazoline-8-carboxamide.

23. A compound in accordance with claim 1, 2-(1-methylethyl)-N-[4-(3-pyridyl)butyl]-11-oxo-11H-pyrido[2,1-b]quinazoline-6-carboxamide.

24. A compound in accordance with claim 1, 2,3-dimethyl-N-[4-(5-pyrimidinyl)butyl]-11-oxo-11H-pyrido[2,1-b]-quinazoline-8-carboxamide.

25. A compound in accordance with claim 1, 2-(1-methylethyl)-N-[4-(1H-imidazol-1-yl)-1-methylbutyl]-11-oxo-11H-pyrido[2,1-b]quinazoline-8-carboxamide.

26. A compound in accordance with claim 1, 2,3-dimethyl-N-[4-(3-pyridinyl)butyl]-11-oxo-11H-pyrido[2,1-b]quinazoline-8-carboxamide.

27. A pharmaceutical composition comprising a compound of the formula

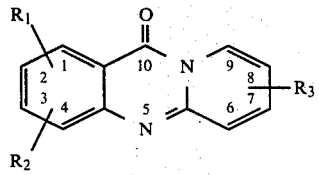

I

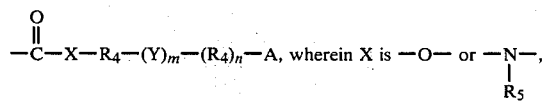

wherein $R_1$ and $R_2$, independently, are hydrogen, lower alkyl, lower alkoxy, hydroxy or halogen, and $R_3$ is in the 6-, 7- or 8-ring position and is wherein $R_5$ is hydrogen or lower alkyl, $R_4$ is lower alkylene, Y is —O— or —S—, m is zero or 1, n is zero or 1, and A is an unsubstituted or substituted aromatic 5- or 6-membered heterocyclic group selected from the group consisting of pyridyl, pyrimidinyl, imidazolyl, furyl, thienyl thiazolyl, oxazolyl, isoxazolyl, pyrazinyl, quinolinyl, isoquinolinyl, quinazolinyl, 1,2,4-triazinyl, 1,2,4-triazolyl, benzimidazolyl and pyridazinyl and wherein the substituents are selected from the group consisting of straight- and branched-chain lower alkyl, straight- and branched-chain lower alkoxy, halogen and nitro, provided that when A is linked through a heterocyclic nitrogen, m and n must each be zero, or a pharmaceutically acceptable acid addition salt thereof, and an inert pharmaceutical carrier material.

28. A method of treating an allergic condition which comprises administering an effective amount of a compound of the formula

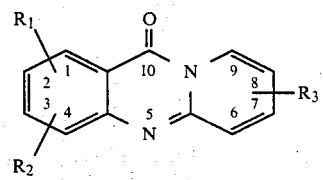

I

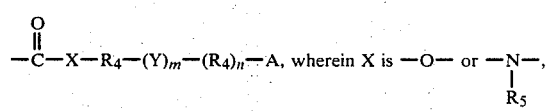

wherein $R_1$ and $R_2$, independently, are hydrogen, lower alkyl, lower alkoxy, hydroxy or halogen, and $R_3$ is in the 6-, 7- or 8-ring position and is wherein $R_5$ is hydrogen or lower alkyl, $R_4$ is lower alkylene, Y is —O— or —S—, m is zero or 1, n is zero or 1, and A is an unsubstituted or substituted aromatic 5- or 6-membered heterocyclic group selected from the group consisting of pyridyl, pyrimidinyl, imidazolyl, furyl, thienyl thiazolyl, oxazolyl, isoxazolyl, pyrazinyl, quinolinyl, isoquinolinyl, quinazolinyl, 1,2,4-triazinyl, 1,2,4-triazolyl, benzimidazolyl and pyridazinyl and wherein the substituents are selected from the group consisting of straight- and branched-chain lower alkyl, straight- and branched-chain lower alkoxy, halogen and nitro, provided that when A is linked through a heterocyclic nitrogen, m and n must each be zero, or a pharmaceutically acceptable acid addition salt thereof.

29. A method of treating a vascular disorder involving thrombosis which comprises administering an effective amount of a compound of the formula

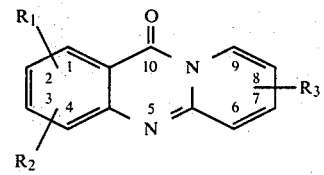

I

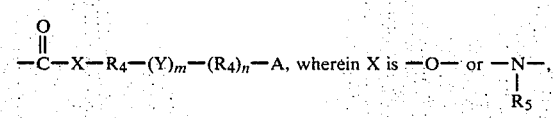

wherein $R_1$ and $R_2$, independently, are hydrogen, lower alkyl, lower alkoxy, hydroxy or halogen, and $R_3$ is in the 6-, 7- or 8-ring position and is wherein $R_5$ is hydrogen or lower alkyl, $R_4$ is lower alkylene, Y is —O— or —S—, m is zero or 1, n is zero or 1, and A is an unsubstituted or substituted aromatic 5- 6-membered heterocyclic group selected from the group consisting of pyridyl, pyrimidinyl, imidazolyl, furyl, thienyl thiazolyl, oxazolyl, isoxazolyl, pyrazinyl, quinolinyl, isoquinolinyl, quinazolinyl, 1,2,4-triazinyl, 1,2,4-triazolyl, benzimidazolyl and pyridazinyl and wherein the substituents are selected from the group consisting of straight- and branched-chain lower alkyl, straight- and branched-chain lower alkoxy, halogen and nitro, provided that when A is linked through a heterocyclic nitrogen, m and n must each be zero, or a pharmaceutically acceptable acid addition salt thereof.

30. A compound of the formula

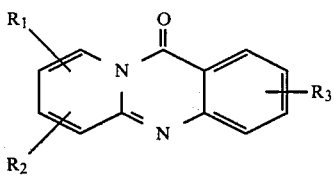

wherein $R_1$ and $R_2$, independently, are hydrogen, lower alkyl, lower alkoxy, hydroxy or halogen, and $R_3$ is in the 2-, 3- or 4-position and is

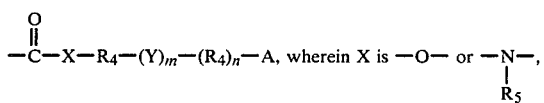

wherein $R_5$ is hydrogen or lower alkyl, $R_4$ is lower alkylene, Y is —O— or —S—, m is zero or 1, n is zero or 1, and A is an unsubstituted or substituted aromatic 5- or 6-membered heterocyclic group selected from the group consisting of pyridyl, pyrimidinyl, imidazolyl, furyl, thienyl thiazolyl, oxazolyl, isoxazolyl, pyrazinyl, quinolinyl, isoquinolinyl, quinazolinyl, 1,2,4-triazinyl, 1,2,4-triazolyl benzimidazolyl and pyridazinyl and wherein the substituents are selected from the group consisting of straight- and branched-chain lower alkyl, straight- and branched-chain lower alkoxy, halogen and nitro, provided that when A is linked through a heterocyclic nitrogen, m and n must each be zero, or a pharmaceutically acceptable acid addition salt thereof.

31. A compound in accordance with claim 30, wherein X is

32. A compound in accordance with claim 31, wherein A is 3-pyridyl, 4-pyridyl or imidazol-1-yl.

33. A compound in accordance with claim 32, wherein $R_1$ is in the 8-position, $R_2$ is in the 7-position, and $R_3$ is in the 2-position.

34. A compound in accordance with claim 33, wherein $R_1$ is lower alkyl, $R_2$ is hydrogen, $R_4$ is lower alkylene of 4-6 carbon atoms, and m and n are zero.

35. A compound in accordance with claim 34, wherein $R_1$ is isopropyl.

36. A compound in accordance with claim 30, 8-(1-methylethyl)-N-[4-(3-pyridyl)butyl]-11-oxo-11H-pyrido[2,1-b]quinazoline-2-carboxamide.

37. A compound in accordance with claim 30, 8-(1-methylethyl)-11-oxo-11H-pyrido[2,1-b]quinazoline-2-carboxylic acid 3-(3-pyridyl)propyl ester.

38. A pharmaceutical composition comprising a compound of the formula

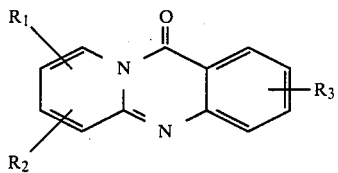

wherein $R_1$ and $R_2$, independently are hydrogen, lower alkyl, lower alkoxy, hydroxy or halogen, and $R_3$ is in the 2-, 3- or 4-position and is

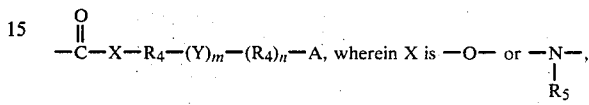

wherein $R_5$ is hydrogen or lower alkyl, $R_4$ is lower alkylene, Y is —O— or —S—, m is zero or 1, n is zero or 1, and A is an unsubstituted or substituted aromatic 5- or 6-membered heterocyclic group selected from the group consisting of pyridyl, pyrimidinyl, imidazolyl, furyl, thienyl thiazolyl, oxazolyl, isoxazolyl, pyrazinyl, quinolinyl, isoquinolinyl, quinazolinyl, 1,2,4-triazinyl, 1,2,4-triazolyl, benzimidazolyl and pyridazinyl and wherein the substituents are selected from the group consisting of straight- and branched-chain lower alkyl, straight- and branched-chain lower alkoxy, halogen and nitro, provided that when A is linked through a heterocyclic nitrogen, m and n must each be zero, or a pharmaceutically acceptable acid addition salt thereof, and an inert pharmaceutical carrier material.

39. A method of treating an allergic condition which comprises administering an effective amount of a compound of the formula

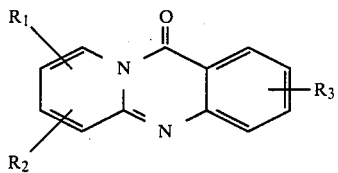

wherein $R_1$ and $R_2$, independently, are hydrogen, lower alkyl, lower alkoxy, hydroxy or halogen, and $R_3$ is in the 2-, 3- or 4-position and is

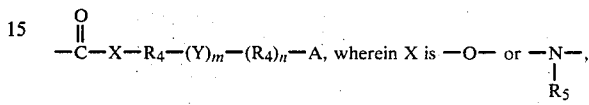

wherein $R_5$ is hydrogen or lower alkyl, $R_4$ is lower alkylene, Y is —O— or —S—, m is zero or 1, n is zero or 1, and A is an unsubstituted or substituted aromatic 5- or 6-membered heterocyclic group selected from the group consisting of pyridyl, pyrimidinyl, imidazolyl, furyl, thienyl thiazolyl, oxazolyl, isoxazolyl, pyrazinyl, quinolinyl, isoquinolinyl, quinazolinyl, 1,2,4-triazinyl, 1,2,4-triazolyl, benzimidazolyl and pyridazinyl wherein the substituents are selected from the group consisting of striaght- and branched-chain lower alkyl, straight- and branched-chain lower alkoxy, halogen and nitro, provided that when A is linked through a heterocyclic nitrogen, m and n must each be zero, or a pharmaceutically acceptable acid addition salt thereof.

40. A method of treating a vascular disorder involving thrombosis which comprises administering an effective amount of a compound of the formula

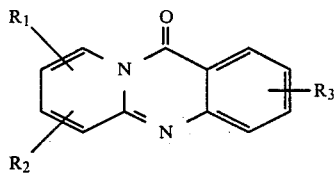

wherein $R_1$ and $R_2$, independently, are hydrogen, lower alkyl, lower alkoxy, hydroxy or halogen, and $R_3$ is in the 2-, 3- or 4-position and is

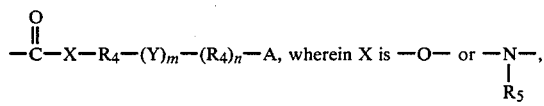

wherein $R_5$ is hydrogen or lower alkyl, $R_4$ is lower alkylene, Y is —O— or —S—, m is zero or 1, n is zero or 1, and A is an unsubstituted or substituted aromatic 5- or 6-membered heterocyclic group selected from the group consisting of pyridyl, pyrimidinyl, imidazolyl, furyl, thienyl, thiazolyl, oxazolyl, isoxazolyl, pyrazinyl, quinolinyl, isoquinolinyl, quinazolinyl, 1,2,4-triazinyl, 1,2,4-triazolyl, benzimidazolyl and pyridazinyl and wherein the substituents are selected from the group consisting of straight- and branched-chain lower alkyl, straight- and branched-chain lower alkoxy, halogen and nitro, provided that when A is linked through a heterocyclic nitrogen, m and n must each be zero, or a pharmaceutically acceptable acid addition salt thereof.

41. A pharmaceutical composition in accordance with claim 27, wherein $R_1$ is isopropyl.

42. A pharmaceutical composition in accordance with claim 27, wherein the compound of formula I is N-[4-(1H-imidazol-1-yl)butyl]-2-(-methylethyl)-11-oxo-11H-pyrido[2,1-b]quinazoline-8-carboxamide.

43. A pharmaceutical composition in accordance with claim 27, wherein the compound of formula I is 2-(1-methylethyl)-N-[4-(3-pyridyl)butyl]-11-oxo-11H-pyrido[2,1-b]quinazoline-8-carboxamide.

44. A pharmaceutical composition in accordance with claim 38, wherein $R_1$ is isopropyl.

45. A pharmaceutical composition in accordance with claim 38, wherein the compound of formula II is 8-(1-methylethyl)-N-[4-(3-pyridyl)butyl]-11-oxo-11H-pyrido[2,1-b]quinazoline-2-carboxamide.

46. A pharmaceutical composition in accordance with claim 38, wherein the compound of formula II, is 8-(1-methylethyl)-11-oxo-11H-pyrido[2,1-b]quinazoline-2-carboxylic acid 3-(3-pyridyl)propyl ester.

47. A method of treating the allergic condition in accordance with claim 28, wherein $R_1$ is isopropyl.

48. A method of treating an allergic condition in accordance with claim 28, wherein the compound of formula 1 is N-[4-(1H-imidazol-1-yl)butyl]-2-(1-methylethyl)-11-oxo-11H-pyrido[2,1-b]quinazoline-8-carboxamide.

49. A method of treating an allergic condition in accordance with claim 28, wherein the compound of formula I is 2-(1-methylethyl)-N-[4-(3-pyridyl)butyl]-11-oxo-11H-pyrido[2,1-b]quinazoline-8-carboxamide.

50. A method of treating an allergic condition in accordance with claim 39 wherein $R_1$ is isopropyl.

51. A method of treating an allergic condition in accordance with claim 39 wherein the compound of formula II is 8-(1-methylethyl)-N-[4-(3-pyridyl)butyl]-11-oxo-11H-pyrido[2,1-b]quinazoline-2-carboxamide.

52. A method of treating an allergic condition in accordance with claim 39 wherein the compound of formula II is 8-(1-methylethyl)-11-oxo-11H-pyrido[2,1-b]quinazoline-2-carboxylic acid 3-(3-pyridyl)propyl ester.

53. A method of treating a vascular disorder involving thrombosis in accordance with claim 29 wherein $R_1$ is isopropyl.

54. A method of treating a vascular disorder involving thrombosis in accordance with claim 29 wherein the compound of formula I is N-[4-(1H-imidazol-1-yl)butyl]-2-(1-methylethyl)-11-oxo-11H-pyrido[2,1-b]quinazoline-8-carboxamide.

55. A method of treating a vascular disorder involving thrombosis in accordance with claim 29 wherein the compound of formula I is 2-(1-methylethyl)-N-[4-(3-pyridyl)butyl]-11-oxo-11H-pyrido[2,1-b]quinazoline-8-carboxamide.

56. A method of treating a vascular disorder involving thrombosis in accordance with claim 40 wherein $R_1$ is isopropyl.

57. A method of treating a vascular disorder involving thrombosis in accordance with claim 40 wherein the compound of formula II is 8-(1-methylethyl)-N-[4-(3-pyridyl)butyl]-11-oxo-11H-pyrido[2,1-b]quinazoline-2-carboxamide.

58. A method of treating a vascular disorder involving thrombosis in accordance with claim 40 wherein the compound of formula II is 8-(1-methylethyl)-11-oxo-11H-pyrido[2,1-b]quinazoline-2-carboxylic acid 3-(3-pyridyl)propyl ester.

* * * * *